US 11,986,645 B2

(12) United States Patent
Toong et al.

(10) Patent No.: US 11,986,645 B2
(45) Date of Patent: May 21, 2024

(54) RESTLESS LEGS SYNDROME TREATMENT SYSTEM

(71) Applicant: Neurostim Technologies LLC, Waltham, MA (US)

(72) Inventors: Hoo-min D. Toong, Cambridge, MA (US); William C. Altmann, Austin, TX (US)

(73) Assignee: Neurostim Technologies LLC, Waltham, MA (US)

( * ) Notice: Subject to any disclaimer, the term of this patent is extended or adjusted under 35 U.S.C. 154(b) by 887 days.

(21) Appl. No.: 17/038,289

(22) Filed: Sep. 30, 2020

(65) Prior Publication Data

US 2021/0023360 A1 Jan. 28, 2021

Related U.S. Application Data

(63) Continuation-in-part of application No. 16/181,929, filed on Nov. 6, 2018, now Pat. No. 10,953,225, and a continuation-in-part of application No. 15/882,213, filed on Jan. 29, 2018, now abandoned.

(60) Provisional application No. 62/907,937, filed on Sep. 30, 2019, provisional application No. 62/661,256, filed on Apr. 23, 2018, provisional application No. 62/582,634, filed on Nov. 7, 2017.

(51) Int. Cl.
*A61N 1/04* (2006.01)
*A61N 1/36* (2006.01)

(52) U.S. Cl.
CPC ......... *A61N 1/0452* (2013.01); *A61N 1/0456* (2013.01); *A61N 1/0492* (2013.01); *A61N 1/36031* (2017.08)

(58) Field of Classification Search
CPC .. A61N 1/0452; A61N 1/0456; A61N 1/0492; A61N 1/36031
See application file for complete search history.

(56) References Cited

U.S. PATENT DOCUMENTS 5,433,737 A 7/1995 Aimone
6,081,744 A 6/2000 Loos
(Continued)

FOREIGN PATENT DOCUMENTS

CN 101868279 A 10/2010
JP 2010004961 A 1/2010
(Continued)

OTHER PUBLICATIONS

Aksu, M, et al.; State dependent excitability changes of spinal flexor reflex in patients with restless legs syndrome secondary to chronic renal failure; Sleep Medicine; 2002; 3(5); 427-430.
(Continued)

*Primary Examiner* — Joseph M Dietrich
(74) *Attorney, Agent, or Firm* — Potomac Law Group, PLLC

(57) ABSTRACT

Example inventions treat restless legs syndrome ("RLS"). Examples affix a patch externally on a dermis of a user adjacent to a targeted nerve of the user, the patch including a flexible substrate, a processor directly coupled to the substrate, and electrodes directly coupled to the substrate. Examples detect the occurrence of RLS and in response to the detecting, activate the patch, the activating including generating an electrical stimuli via the electrodes that is directed to the targeted nerve.

18 Claims, 18 Drawing Sheets

(56) References Cited

U.S. PATENT DOCUMENTS

| | | | |
|---|---|---|---|
| 6,155,976 | A | 12/2000 | Sackner et al. |
| 6,819,956 | B2 | 11/2004 | DiLorenzo |
| 7,616,988 | B2 | 11/2009 | Stahmann et al. |
| 7,643,874 | B2 | 1/2010 | Nitzan et al. |
| 7,689,285 | B2 | 3/2010 | Garabet |
| 7,887,493 | B2 | 2/2011 | Stahmann et al. |
| 7,922,676 | B2 | 4/2011 | Daskal et al. |
| 7,974,696 | B1 | 7/2011 | DiLorenzo |
| 8,386,032 | B2 | 2/2013 | Bachinski et al. |
| 8,498,698 | B2 | 7/2013 | Donofrio et al. |
| 8,538,543 | B2 | 9/2013 | McIntyre et al. |
| 8,657,756 | B2 | 2/2014 | Stahmann et al. |
| 8,688,190 | B2 | 4/2014 | Libbus et al. |
| 8,818,515 | B2 | 8/2014 | Bikson et al. |
| 9,302,107 | B2 | 4/2016 | Lauritzen et al. |
| 9,307,925 | B2 | 4/2016 | Russell et al. |
| 9,855,427 | B2 | 1/2018 | Bennett et al. |
| 10,342,977 | B2 | 7/2019 | Raghunathan |
| 10,576,277 | B2 | 3/2020 | Morriss et al. |
| 10,737,096 | B1 | 8/2020 | Klee |
| 10,767,096 | B2 | 9/2020 | Amanullah |
| 2002/0019652 | A1 | 2/2002 | Silva et al. |
| 2004/0049241 | A1 | 3/2004 | Campos |
| 2004/0133164 | A1 | 7/2004 | Funderburk et al. |
| 2006/0004424 | A1 | 1/2006 | Loeb et al. |
| 2008/0027507 | A1 | 1/2008 | Bijelic et al. |
| 2008/0149102 | A1 | 6/2008 | Kim et al. |
| 2008/0161887 | A1 | 7/2008 | Hagen |
| 2009/0048643 | A1 | 2/2009 | Erickson et al. |
| 2009/0132018 | A1 | 5/2009 | DiUbaldi et al. |
| 2009/0149912 | A1 | 6/2009 | Dacey, Jr. et al. |
| 2009/0182393 | A1 | 7/2009 | Bachinski |
| 2010/0204538 | A1 | 8/2010 | Burnett et al. |
| 2010/0249637 | A1 | 9/2010 | Walter et al. |
| 2010/0261994 | A1 | 10/2010 | Davalos et al. |
| 2011/0160806 | A1 | 6/2011 | Lyden et al. |
| 2012/0123508 | A1 | 5/2012 | Wentz et al. |
| 2012/0283800 | A1 | 11/2012 | Perryman et al. |
| 2013/0030257 | A1 | 1/2013 | Nakata et al. |
| 2013/0035745 | A1 | 2/2013 | Ahmed et al. |
| 2013/0060149 | A1 | 3/2013 | Song et al. |
| 2013/0226261 | A1 | 8/2013 | Sparks et al. |
| 2014/0046423 | A1* | 2/2014 | Rajguru ............... A61N 2/02 607/144 |
| 2014/0194951 | A1 | 7/2014 | Gong et al. |
| 2014/0228927 | A1 | 8/2014 | Ahmad et al. |
| 2014/0324120 | A1 | 10/2014 | Bogie et al. |
| 2015/0148869 | A1 | 5/2015 | Dorvall et al. |
| 2015/0164401 | A1 | 6/2015 | Toth et al. |
| 2015/0335876 | A1 | 11/2015 | Jeffery et al. |
| 2015/0335877 | A1 | 11/2015 | Jeffery et al. |
| 2015/0335888 | A1 | 11/2015 | Demers et al. |
| 2016/0015962 | A1 | 1/2016 | Maragheh et al. |
| 2016/0213922 | A1 | 7/2016 | Goldberg et al. |
| 2016/0263376 | A1 | 9/2016 | Yoo et al. |
| 2016/0314282 | A1 | 10/2016 | Klee |
| 2016/0346530 | A1 | 12/2016 | Jeffery et al. |
| 2017/0001003 | A1 | 1/2017 | Pivonka et al. |
| 2017/0095667 | A1 | 4/2017 | Yakovlev et al. |
| 2017/0215745 | A1 | 8/2017 | Felix et al. |
| 2017/0224990 | A1 | 8/2017 | Goldwasser et al. |
| 2017/0312512 | A1 | 11/2017 | Creasey et al. |
| 2017/0312526 | A1 | 11/2017 | Steinke et al. |
| 2017/0333695 | A1 | 11/2017 | Kaplan et al. |
| 2018/0020951 | A1 | 1/2018 | Kaifosh et al. |
| 2018/0116877 | A1 | 5/2018 | Ineichen |
| 2018/0133479 | A1 | 5/2018 | Bennett et al. |
| 2018/0140859 | A1 | 5/2018 | Meir |
| 2018/0154147 | A1 | 6/2018 | Izvorski et al. |
| 2018/0161586 | A1 | 6/2018 | Beyer et al. |
| 2018/0214054 | A1 | 8/2018 | Soltani et al. |
| 2018/0318585 | A1 | 11/2018 | Pfeifer |
| 2018/0350451 | A1 | 12/2018 | Ohnemus et al. |
| 2019/0114766 | A1 | 4/2019 | Song et al. |
| 2019/0117976 | A1 | 4/2019 | Belson et al. |
| 2019/0134391 | A1 | 5/2019 | Druke et al. |
| 2019/0134396 | A1 | 5/2019 | Toth et al. |
| 2019/0189253 | A1 | 6/2019 | Kartoun et al. |
| 2019/0198144 | A1 | 6/2019 | Blackley et al. |
| 2019/0282822 | A1 | 9/2019 | Freeman et al. |
| 2019/0313934 | A1 | 10/2019 | Lee et al. |
| 2019/0336763 | A1 | 11/2019 | Spurling et al. |
| 2020/0069941 | A1 | 3/2020 | Campean et al. |
| 2020/0069942 | A1 | 3/2020 | Campean et al. |
| 2020/0139118 | A1 | 5/2020 | John et al. |
| 2020/0338333 | A1 | 10/2020 | Toong et al. |
| 2020/0338334 | A1 | 10/2020 | Toong et al. |
| 2020/0376266 | A1 | 12/2020 | Toong et al. |

FOREIGN PATENT DOCUMENTS

| | | |
|---|---|---|
| JP | 2011502707 A | 1/2011 |
| WO | 2009064641 A1 | 5/2009 |
| WO | 2011053607 A1 | 5/2011 |
| WO | 2014194200 A1 | 12/2014 |
| WO | 2015183620 A2 | 12/2015 |
| WO | 2017178946 A1 | 10/2017 |

OTHER PUBLICATIONS

Bucher, SF, et al.; Reflex studies and MRI in the restless legs syndrome; Acta Neurologica Scandinavica; 1996; 94(2); 145-150.

Cogiamanian, F, et al.; Transcutaneous spinal cord direct current stimulation inhibits the lower limb nociceptive flexion reflex in human beings; Pain; 2011; 152(2); 370-375.

Dafkin, C, et al.; Circadian variation of flexor withdrawal and crossed extensor reflexes in patients with restless legs syndrome; Journal of Sleep Research; 2018; 27(5); 1-7.

Entezari-Taher, M, et al.; Changes in excitability of motor cortical circuitry in primary restless legs syndrome; Neurology; 1999; 53(6); 1201-1205.

Garrison, MK, et al.; Flexor reflex decreases during sympathetic stimulation in chronic human spinal cord injury; Experimental Neurology; 2009; 219(2); 507-515.

Gemignani, F; Restless legs syndrome from the spinal cord perspective: A flexor reflex circuitopathy ?; Journal of Sleep Research; 2018; 27(5); 1-2.

Gregori?, M; Suppression of flexor reflex by transcutaneous electrical nerve stimulation in spinal cord injured patients; Muscle and Nerve; 1998; 21(2); 166-172.

Guo, S, et al.; Restless legs syndrome: From pathophysiology to clinical diagnosis and management; Frontiers in Aging Neuroscience; 2017; 9(JUN); 1-14.

Heide, AC, et al.; Effects of transcutaneous spinal direct current stimulation in idiopathic restless legs patients; Brain Stimulation; 2014; 7(5); 636-642.

Karatas, M; Restless legs syndrome and periodic limb movements during sleep: Diagnosis and treatment; Neurologist; 2007; 13(5); 294-301.

Koo, BB, et al.; Restless Legs Syndrome: Current Concepts about Disease Pathophysiology; Tremor and Other Hyperkinetic Movements; 2016; 6(0); 401.

Kova?evi?- Ristanovi?, R, et al.; Nonpharmacologic treatment of periodic leg movements in sleep; Archives of Physical Medicine and Rehabilitation; 1991; 72(6); 385-389.

Krueger, BR; Restless Legs Syndrome and Periodic Movements of Sleep; Mayo Clinic Proceedings; 1990; 65(7); 999-1006.

Merkl, A, et al.; Vagus nerve stimulation improves restless legs syndrome associated with major depression: A case report [3]; Journal of Clinical Psychiatry; 2007; 68(4); 635-636.

Ninds, S, et al.; Restless Legs Syndrome Fact Sheet Restless Legs Syndrome Fact Sheet What is restless legs syndrome??; 2019; 1-8.

Raissi, GR, et al.; Evaluation of Acupuncture in the Treatment of Restless Legs Syndrome: A Randomized Controlled Trial; JAMS Journal of Acupuncture and Meridian Studies; 2017; 10(5); 346-350.

Rizzo, V, et al.; Dopamine agonists restore cortical plasticity in patients with idiopathic restless legs syndrome; Movement Disorders; 2009; 24(5); 710-715.

(56) References Cited

OTHER PUBLICATIONS

Roby-Brami, A, et al.; Inhibitory effects on flexor reflexes in patients with a complete spinal cord lesion; Experimental Brain Research; 1992; 90(1); 201-208.

Rozeman, AD, et al.; Effect of sensory stimuli on restless legs syndrome: A randomized crossover study; Journal of Clinical Sleep Medicine; 2014; 10(8); 893-896.

Sharon, D, et al.; Restless Legs Syndrome and Periodic Limb Movement Disorder in Children; Journal of Child Science; 2019; 9(1); E38-E49.

Yam, MF, et al.; General pathways of pain sensation and the major neurotransmitters involved in pain regulation; International Journal of Molecular Sciences; 2018; 19(8).

Yogi A. Patel; Kilohertz Electrical Stimulation Nerve Conduction Block: Effects of Electrode Surface Area; IEEE Transactions on Neural Systems and Rehabilitation Engineering, vol. 25, No. 10, Oct. 2017.

Patel, Kilhertz Electrical Stimulation Nerve Conduction Block: Effects of Electrode Surface Area, IEEE Transactions on Neural Systems and Rehabilitation Engineering, vol. 25, No. 10, Oct. 2017.

\* cited by examiner

| Frequency | Duration | | | | | |
|---|---|---|---|---|---|---|
| | 1 | 5 | 10 | 20 | 30 | 50 |
| 1 | 1 | 5 | 10 | 20 | 30 | 50 |
| 5 | 5 | 25 | 50 | 100 | 150 | 250 |
| 20 | 20 | 100 | 200 | 400 | 600 | 1000 |
| 50 | 50 | 250 | 500 | 1000 | 1500 | 2500 |
| 100 | 100 | 500 | 1000 | 2000 | 3000 | 5000 |
| 150 | 150 | 750 | 1500 | 3000 | 4500 | 7500 |

Fig. 7

RESTLESS LEGS SYNDROME TREATMENT SYSTEM

CROSS REFERENCE TO RELATED APPLICATIONS

This application claims priority to U.S. Provisional Patent Application Ser. No. 62/907,937, filed on Sep. 30, 2019, and claims priority as a continuation-in-part application to U.S. patent application Ser. No. 16/181,929, filed on Nov. 6, 2018, which claims priority to U.S. Provisional Patent Application Ser. No. 62/582,634, filed on Nov. 7, 2017, and to U.S. Provisional Patent Application Ser. No. 62/661,256, filed on Apr. 23, 2018, and claims priority as a continuation-in-part application of U.S. patent application Ser. No. 15/882,213, filed on Jan. 29, 2018, which claims priority to U.S. Provisional Patent Application Ser. No. 62/582,634, filed on Nov. 7, 2017. The disclosure of each of these applications is hereby incorporated by reference.

FIELD

Example inventions are directed to systems and methods for improving rest and sleep by treating the effects of Restless Legs Syndrome.

BACKGROUND INFORMATION

Restless legs syndrome ("RLS"), also referred to as "Willis-Ekbom" disease is generally a long-term disorder that causes a strong urge to move one's legs. There is often an unpleasant feeling in the legs that improves somewhat by moving them. This is often described as aching, tingling, or crawling in nature. Occasionally, arms may also be affected. The feelings generally happen when at rest and therefore can make it hard to sleep. Due to the disturbance in sleep, people with RLS may have daytime sleepiness, low energy, irritability and a depressed mood. Additionally, many have limb twitching during sleep.

Similar to RLS, Periodic Limb Movement ("PLM") disorder, in two forms as Periodic Limb Movement while Awake ("PLMA") and Periodic Limb Movement while Asleep ("PLMS") include common symptoms of involuntary leg movement while awake and preparing to sleep (PLMA) and while asleep (PLMS). Each of PLMA and PLMS affect restfulness, which in turn affects mood, alertness, concentration and relationships while awake.

BRIEF DESCRIPTION OF THE DRAWINGS

FIG. 7 is a table relating charge duration vs. frequency to provide feedback to the adaptive protocol in accordance with one example.

DETAILED DESCRIPTION

A non-invasive nerve patch/activator in accordance with various examples disclosed herein includes novel circuitry to adequately boost voltage to a required level and to maintain a substantially constant level of charge for nerve activation. Further, a feedback loop provides for an automatic determination and adaptation of the applied charge level. In example inventions, the patch is used to treat the effects of RLS and PLM without the use of medications or surgically implanted devices.

Figure 1:
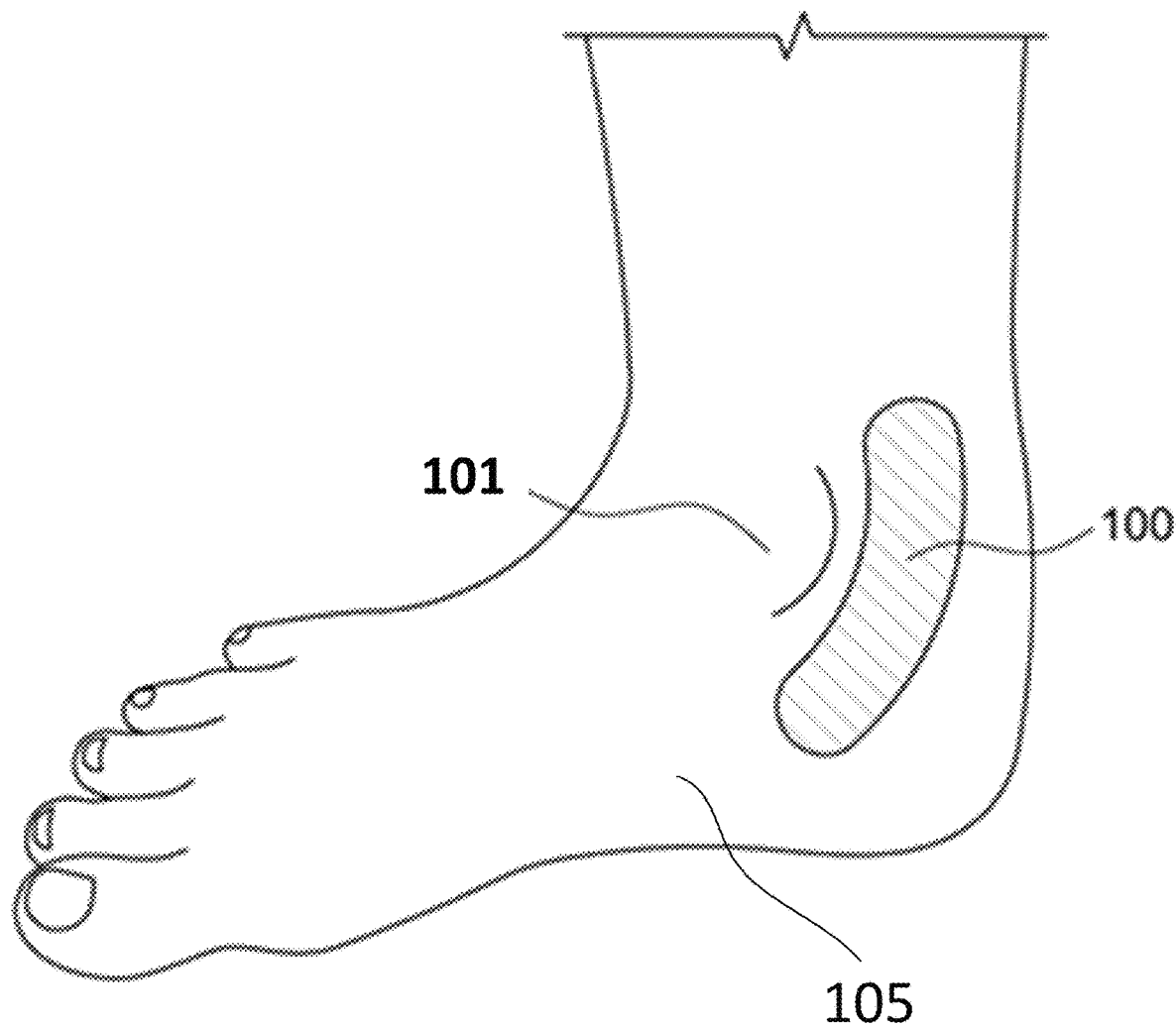
FIG. 1 illustrates an example patch that is affixed to a location behind an ankle bone of a user.

FIG. 1 illustrates an example patch 100, also referred to as a smart band aid or smartpad or Topical Nerve Activator ("TNA") or topical nerve activation patch, that is affixed to a location behind an ankle bone 101 of a user 105 in one example use. In the example of FIG. 1, patch 100 is adapted to activate/stimulate the tibial nerve of user 105. In other examples, patch 100 is worn at different locations of user 105 to activate the tibial nerve from a different location, or to activate a different nerve of user 105.

Patch 100 is used to stimulate these nerves and is convenient, unobtrusive, self-powered, and may be controlled from a smartphone or other control device. This has the advantage of being non-invasive, controlled by consumers themselves, and potentially distributed over the counter without a prescription. Patch 100 provides a means of stimulating nerves without penetrating the dermis, and can be applied to the surface of the dermis at a location appropriate for the nerves of interest. In examples, patch 100 is applied by the user and is disposable.

Patch 100 in examples can be any type of device that can be fixedly attached to a user, using adhesive in some examples, and includes a processor/controller and instructions that are executed by the processor, or a hardware implementation without software instructions, as well as electrodes that apply an electrical stimulation to the surface of the user's skin, and associated electrical circuitry. Patch 100 in one example provides topical nerve activation/stimulation on the user to provide benefits to the user, including bladder management for an overactive bladder ("OAB") or treating the effects of RLS and PLM.

Patch 100 in one example can include a flexible substrate, a malleable dermis conforming bottom surface of the substrate including adhesive and adapted to contact the dermis, a flexible top outer surface of the substrate approximately parallel to the bottom surface, one or more electrodes positioned on the patch proximal to the bottom surface and located beneath the top outer surface and directly contacting the flexible substrate, electronic circuitry (as disclosed herein) embedded in the patch and located beneath the top outer surface and integrated as a system on a chip that is directly contacting the flexible substrate, the electronic circuitry integrated as a system on a chip and including an electrical signal generator integral to the malleable dermis conforming bottom surface configured to electrically activate the one or more electrodes, a signal activator coupled to the electrical signal generator, a nerve stimulation sensor that provides feedback in response to a stimulation of one or more nerves, an antenna configured to communicate with a remote activation device, a power source in electrical communication with the electrical signal generator, and the signal activator, where the signal activator is configured to activate in response to receipt of a communication with the activation device by the antenna and the electrical signal generator configured to generate one or more electrical stimuli in response to activation by the signal activator, and the electrical stimuli configured to stimulate one or more nerves of a user wearing patch 100 at least at one location proximate to patch 100. Additional details of examples of patch 100 beyond the novel details disclosed herein are disclosed in U.S. Pat. No. 10,016,600, entitled "Topical Neurological Stimulation", the disclosure of which is hereby incorporated by reference.

Figure 2:
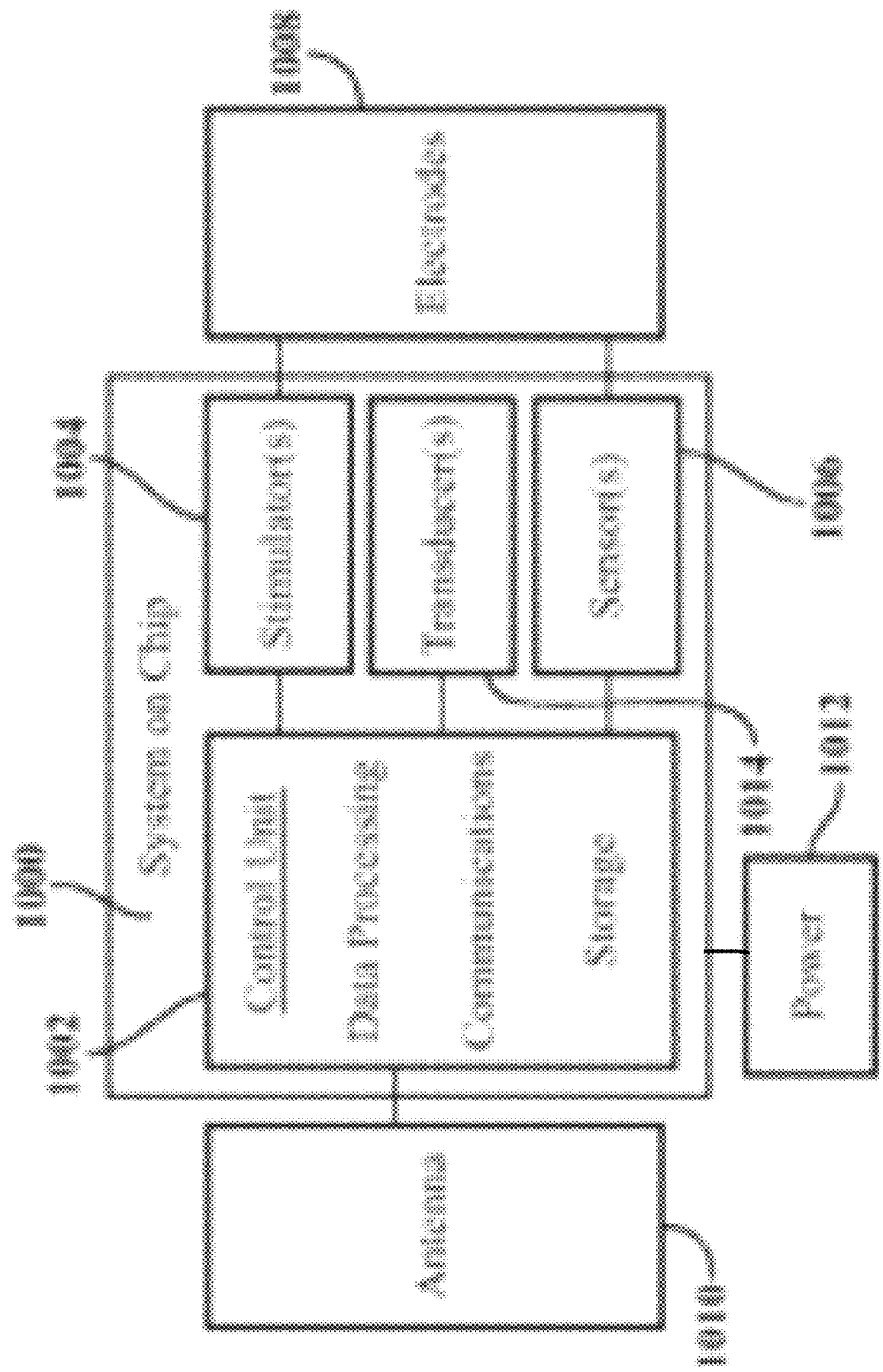
FIG. 2 is a block diagram illustrating hardware/software related elements of an example of the patch of FIG. 1.

FIG. 2 is a block diagram illustrating hardware/software related elements of an example of patch 100 of FIG. 1. Patch 100 includes electronic circuits or chips 1000 that perform the functions of: communications with an external control device, such as a smartphone or fob, or external processing such as cloud based processing devices, nerve activation via electrodes 1008 that produce a wide range of electric fields according to a treatment regimen, and a wide range of sensors 1006 such as, but not limited to, mechanical motion and pressure, temperature, humidity, acoustic, chemical and positioning sensors. In another example, patch 100 includes transducers 1014 to transmit signals to the tissue or to receive signals from the tissue.

One arrangement is to integrate a wide variety of these functions into a system on a chip 1000. Within this is shown a control unit 1002 for data processing, communications, transducer interface and storage, and one or more stimulators 1004 and sensors 1006 that are connected to electrodes 1008. Control unit 1002 can be implemented by a general purpose processor/controller, or a specific purpose processor/controller, or a special purpose logical circuit. An antenna 1010 is incorporated for external communications by control unit 1002. Also included is an internal power supply 1012, which may be, for example, a battery. Other examples may include an external power supply. It may be necessary to include more than one chip to accommodate a wide range of voltages for data processing and stimulation. Electronic circuits and chips will communicate with each other via conductive tracks within the device capable of transferring data and/or power.

Patch 100 interprets a data stream from control unit 1002 to separate out message headers and delimiters from control instructions. In one example, control instructions include information such as voltage level and pulse pattern. Patch 100 activates stimulator 1004 to generate a stimulation signal to electrodes 1008 placed on the tissue according to the control instructions. In another example, patch 100 activates transducer 1014 to send a signal to the tissue. In another example, control instructions cause information such as voltage level and a pulse pattern to be retrieved from a library stored by patch 100, such as storage within control unit 1002.

Patch 100 receives sensory signals from the tissue and translates them to a data stream that is recognized by control unit 1002. Sensory signals can include electrical, mechanical, acoustic, optical and chemical signals. Sensory signals are received by patch 100 through electrodes 1008 or from other inputs originating from mechanical, acoustic, optical, or chemical transducers. For example, an electrical signal from the tissue is introduced to patch 100 through electrodes 1008, is converted from an analog signal to a digital signal and then inserted into a data stream that is sent through antenna 1010 to the external control device. In another example an acoustic signal is received by transducer 1014, converted from an analog signal to a digital signal and then inserted into a data stream that is sent through the antenna 1010 to the external control device. In some examples, sensory signals from the tissue are directly interfaced to the external control device for processing.

In examples of patch 100 disclosed above, when being used for therapeutic treatment such as bladder management for OAB or treatment of RLS/PLM, there is a need to control the voltage by boosting the voltage to a selected level and providing the same level of charge upon activation to a mammalian nerve. Further, there is a need to conserve battery life by selectively using battery power. Further, there is a need to create a compact electronics package to facilitate mounting the electronics package on a relatively small mammalian dermal patch in the range of the size of an ordinary band aid.

Adaptive Circuit

Figure 3A:
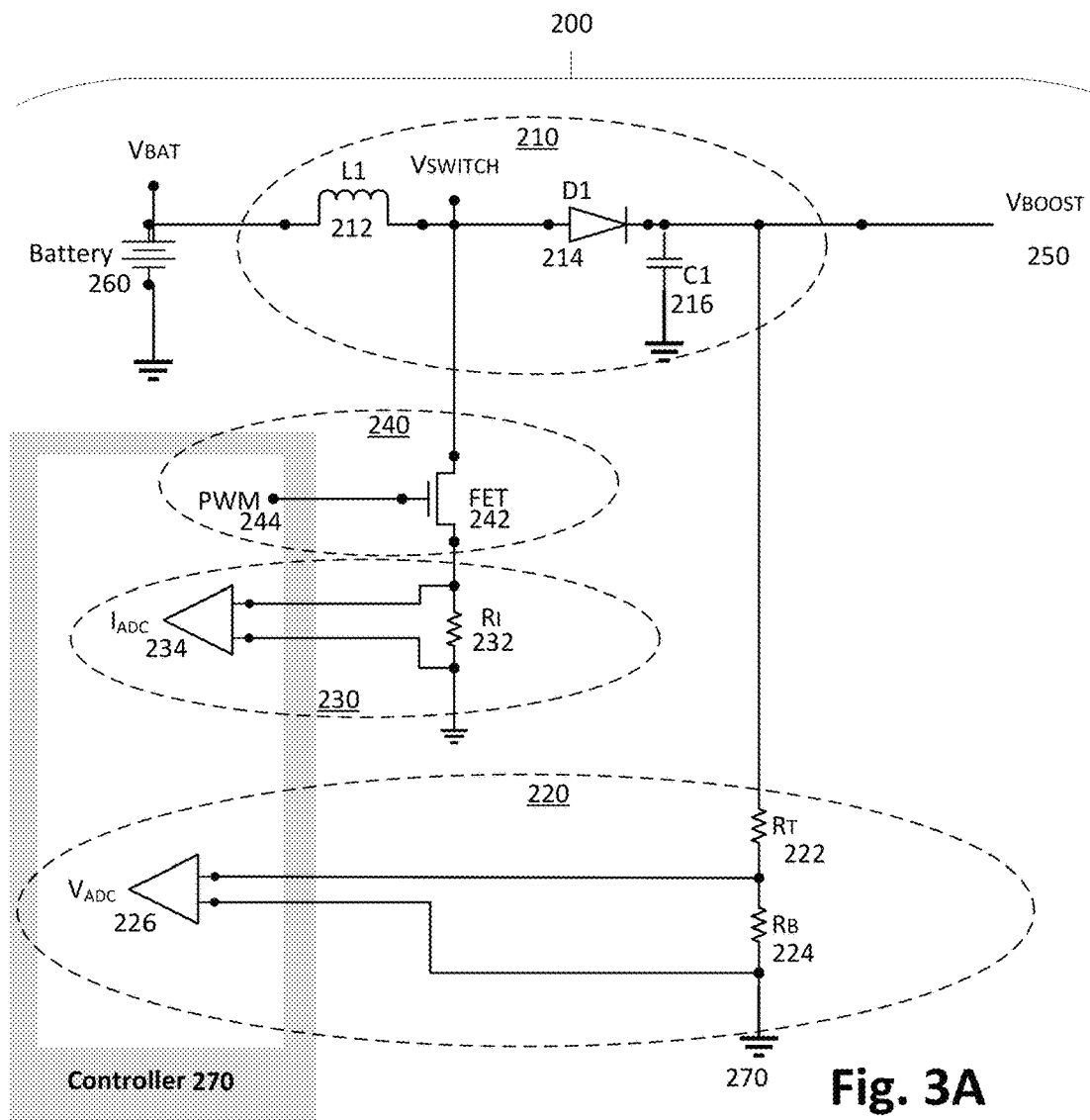
FIG. 3A is a circuit diagram of an example of a boosted voltage circuit that provides feedback.
Figure 3B:
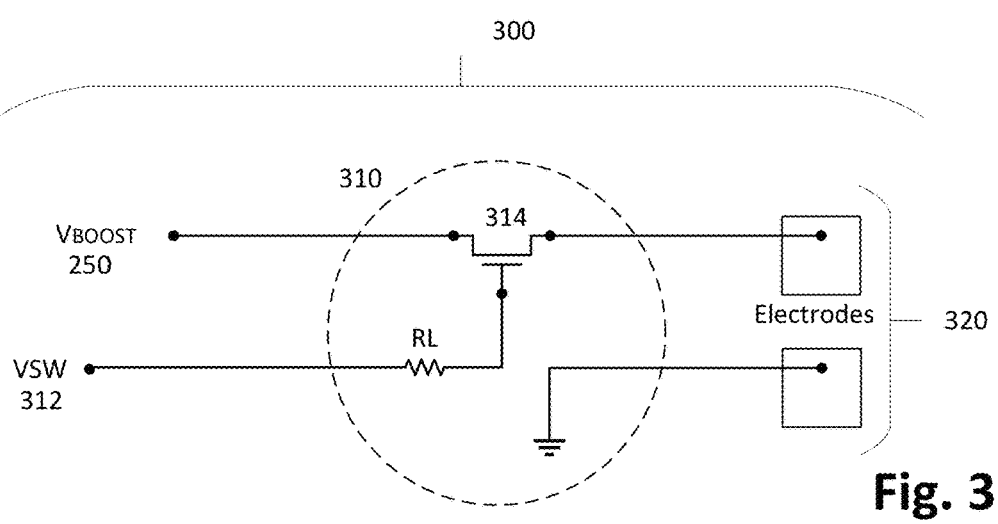
FIG. 3B is a circuit diagram of an example of a charge application circuit that uses an output of the boosted voltage circuit.

To meet the above needs, examples implement a novel boosted voltage circuit that includes a feedback circuit and a charge application circuit. FIG. 3A is a circuit diagram of an example of the boosted voltage circuit 200 that provides feedback. FIG. 3B is a circuit diagram of an example of a charge application circuit 300 that uses an output of boosted voltage circuit 200. Boosted voltage circuit 200 includes both electrical components and a controller/processor 270 that includes a sequence of instructions that together modify the voltage level of activation/stimulation delivered to the external dermis of user 105 by patch 100 through electrodes. Controller/processor 270 in examples implements control unit 1002 of FIG. 2.

Boosted voltage circuit 200 can replace an independent analog-controlled boost regulator by using a digital control loop to create a regulated voltage, output voltage 250, from the battery source. Output voltage 250 is provided as an input voltage to charge application circuit 300. In examples, this voltage provides nerve stimulation currents through the dermis/skin to deliver therapy for an overactive bladder. Output voltage 250, or "$V_{Boost}$", at voltage output node 250, uses two digital feedback paths 220, 230, through controller 270. In each of these paths, controller 270 uses sequences of instructions to interpret the measured voltages at voltage monitor 226, or "$V_{ADC}$" and current monitor 234, or "$I_{ADC}$", and determines the proper output control for accurate and stable output voltage 250.

Boosted voltage circuit 200 includes an inductor 212, a diode 214, a capacitor 216 that together implement a boosted converter circuit 210. A voltage monitoring circuit 220 includes a resistor divider formed by a top resistor 222, or "$R_T$", a bottom resistor 224, or "$R_B$," and voltage monitor 226. A current monitoring circuit 230 includes a current measuring resistor 232, or "$R_I$" and current monitor 234. A pulse width modulation ("PWM") circuit 240 includes a field-effect transistor ("FET") switch 242, and a PWM driver 244. Output voltage 250 functions as a sink for the electrical energy. An input voltage 260, or "$V_{BAT}$", is the source for the electrical energy, and can be implemented by power 1012 of FIG. 2.

PWM circuit 240 alters the "on" time within a digital square wave, fixed frequency signal to change the ratio of time that a power switch is commanded to be "on" versus "off." In boosted voltage circuit 200, PWM driver 244 drives FET switch 242 to "on" and "off" states.

In operation, when FET switch 242 is on, i.e., conducting, the drain of FET switch 242 is brought down to Ground/GND or ground node 270. FET switch 242 remains on until its current reaches a level selected by controller 270 acting as a servo controller. This current is measured as a representative voltage on current measuring resistor 232 detected by current monitor 234. Due to the inductance of inductor 212, energy is stored in the magnetic field within inductor 212. The current flows through current measuring resistor 232 to ground until FET switch 242 is opened by PWM driver 244.

When the intended pulse width duration is achieved, controller 270 turns off FET switch 242. The current in inductor 212 reroutes from FET switch 242 to diode 214, causing diode 214 to forward current. Diode 214 charges capacitor 216. Therefore, the voltage level at capacitor 216 is controlled by controller 270.

Output voltage 250 is controlled using an outer servo loop of voltage monitor 226 and controller 270. Output voltage 250 is measured by the resistor divider using top resistor 222, bottom resistor 224, and voltage monitor 226. The values of top resistor 222 and bottom resistor 224 are selected to keep the voltage across bottom resistor 224 within the monitoring range of voltage monitor 226. Controller 270 monitors the output value from voltage monitor 226.

Charge application circuit 300 includes a pulse application circuit 310 that includes an enable switch 314. Controller 270 does not allow enable switch 314 to turn on unless output voltage 250 is within a desired upper and lower range of the desired value of output voltage 250. Pulse application circuit 310 is operated by controller 270 by asserting an enable signal 312, or "VSW", which turns on enable switch 314 to pass the electrical energy represented by output voltage 250 through electrodes 320. At the same time, controller 270 continues to monitor output voltage 250 and controls PWM driver 244 to switch FET switch 242 on and off and to maintain capacitor 216 to the desired value of output voltage 250.

The stability of output voltage 250 can be increased by an optional inner feedback loop through FET Switch 242, current measuring resistor 232, and current monitor 234. Controller 270 monitors the output value from current monitor 234 at a faster rate than the monitoring on voltage monitor 226 so that the variations in the voltages achieved at the cathode of diode 214 are minimized, thereby improving control of the voltage swing and load sensitivity of output voltage 250.

In one example, a voltage doubler circuit is added to boosted voltage circuit 200 to double the high voltage output or to reduce voltage stress on FET 242. The voltage doubler circuit builds charge in a transfer capacitor when FET 242 is turned on and adds voltage to the output of boosted voltage circuit 200 when FET 242 is turned off.

As described, in examples, controller 270 uses multiple feedback loops to adjust the duty cycle of PWM driver 244 to create a stable output voltage 250 across a range of values. Controller 270 uses multiple feedback loops and monitoring circuit parameters to control output voltage 250 and to evaluate a proper function of the hardware. Controller 270 acts on the feedback and monitoring values in order to provide improved patient safety and reduced electrical hazard by disabling incorrect electrical functions.

In some examples, controller 270 implements the monitoring instructions in firmware or software code. In some examples, controller 270 implements the monitoring instructions in a hardware state machine.

In some examples, voltage monitor 226 is an internal feature of controller 270. In some examples, voltage monitor 226 is an external component, which delivers its digital output value to a digital input port of controller 270.

In some examples, current monitor 234 is an internal feature of controller 270. In some examples, current monitor 234 is an external component, which delivers its digital output value to a digital input port of controller 270.

An advantage of boosted voltage circuit 200 over known circuits is decreased component count which may result in reduced costs, reduced circuit board size and higher reliability. Further, boosted voltage circuit 200 provides for centralized processing of all feedback data which leads to faster response to malfunctions. Further, boosted voltage circuit 200 controls outflow current from $V_{BAT}$ 260, which increases the battery's lifetime and reliability.

Figure 4:
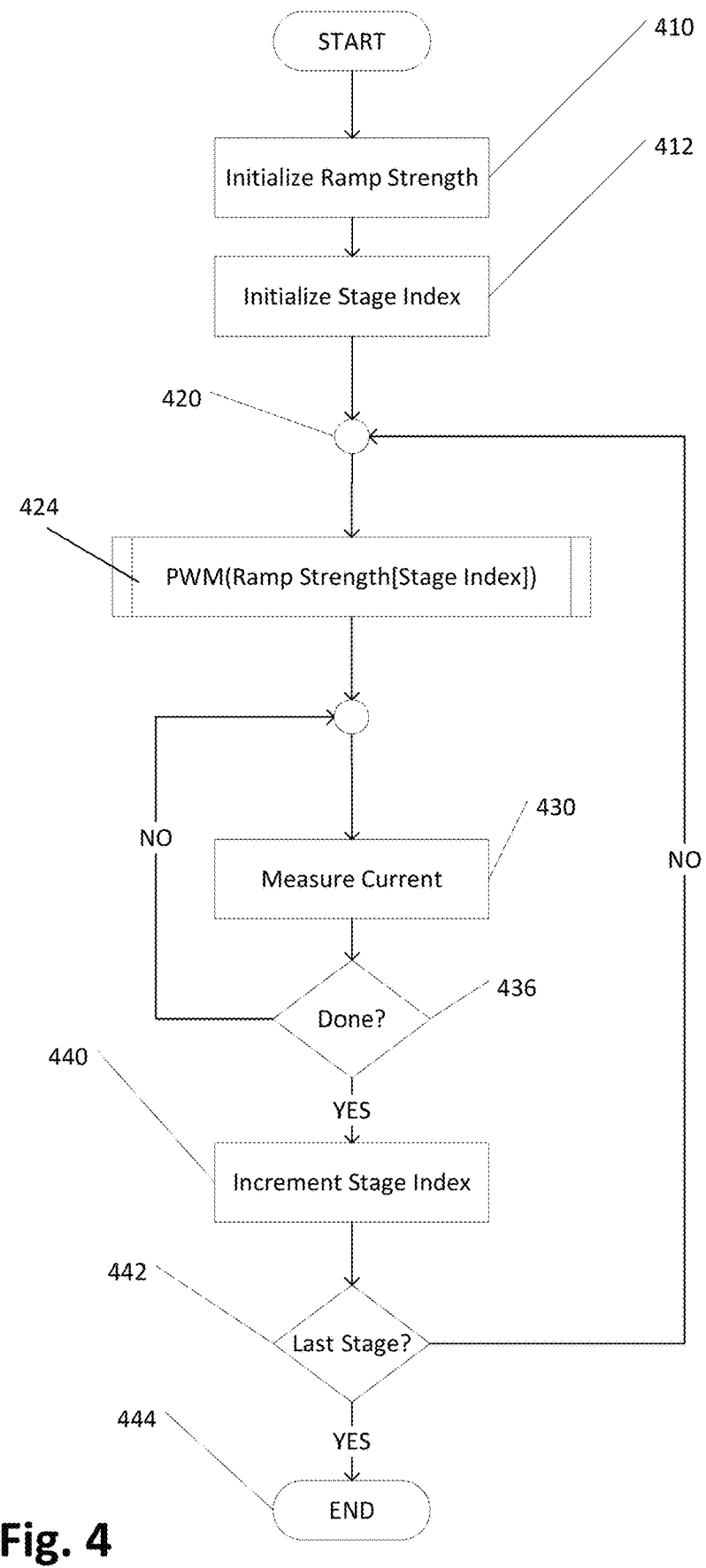
FIG. 4 is a flow diagram of the functionality of the controller of monitoring and controlling the output voltage, including its ramp rate.

FIG. 4 is a flow diagram of the functionality of controller 270 of monitoring and controlling output voltage 250, including its ramp rate. In one example, the functionality of the flow diagram of FIG. 4, and FIG. 5 below, is implemented by software stored in memory or other computer readable or tangible medium, and executed by a processor. In other examples, the functionality may be performed by hardware (e.g., through the use of an application-specific integrated circuit ("ASIC"), a programmable gate array ("PGA"), a field programmable gate array ("FPGA"), etc.), or any combination of hardware and software.

The pulse width modulation of FET switch 242 is controlled by one or more pulses for which the setting of each pulse width allows more or less charge to accumulate as a voltage at capacitor 216 through diode 214. This pulse width setting is referred to as the ramp strength and it is initialized at 410. Controller 270 enables each pulse group in sequence with a pre-determined pulse width, one stage at a time, using a stage index that is initialized at 412. The desired ramp strength is converted to a pulse width at 424, which enables and disables FET switch 242 according to the pulse width. During the intervals when FET switch 242 is "on", the current is measured by current monitor 234 at 430 and checked against the expected value at 436. When the current reaches the expected value, the stage is complete and the stage index is incremented at 440. If the desired number of stages have been applied 442, then the functionality is complete. Otherwise, the functionality continues to the next stage at 420.

As a result of the functionality of FIG. 4, $V_{BAT}$ 260 used in patch 100 operates for longer periods as the current drawn from the battery ramps at a low rate of increase to reduce the peak current needed to achieve the final voltage level 250 for each activation/stimulation treatment. PWM 244 duty cycle is adjusted by controller 270 to change the ramp strength at 410 to improve the useful life of the battery.

An open loop protocol to control current to electrodes in known neural stimulation devices does not have feedback controls. It commands a voltage to be set, but does not check the actual current delivered. A stimulation pulse is sent based on preset parameters and cannot be modified based on feedback from the patient's anatomy. When the device is removed and repositioned, the electrode placement varies. Also the humidity and temperature of the anatomy changes throughout the day. All these factors affect the actual charge delivery if the voltage is preset. Charge control is a patient safety feature and facilitates an improvement in patient comfort, treatment consistency and efficacy of treatment.

In contrast, examples of patch 100 includes features that address these shortcomings using controller 270 to regulate the charge applied by electrodes 320. Controller 270 samples the voltage of the stimulation waveform, providing feedback and impedance calculations for an adaptive protocol to modify the stimulation waveform in real time. The current delivered to the anatomy by the stimulation waveform is integrated using a differential integrator and sampled and then summed to determine the actual charge delivered to the user for a treatment, such as OAB or RLS treatment. After every pulse in a stimulation event, this data is analyzed and used to modify, in real time, subsequent pulses.

This hardware adaptation allows a firmware protocol to implement the adaptive protocol. This protocol regulates the charge applied to the body by changing output voltage ("$V_{BOOST}$") 250. A treatment is performed by a sequence of periodic pulses, which deliver charge into the body through electrodes 320. Some of the parameters of the treatment are fixed and some are user adjustable. The strength, duration and frequency may be user adjustable. The user may adjust these parameters as necessary for comfort and efficacy. The strength may be lowered if there is discomfort and raised if nothing is felt. The duration can be increased if the maximum acceptable strength results in an ineffective treatment.

Adaptive Protocol

Figure 5:
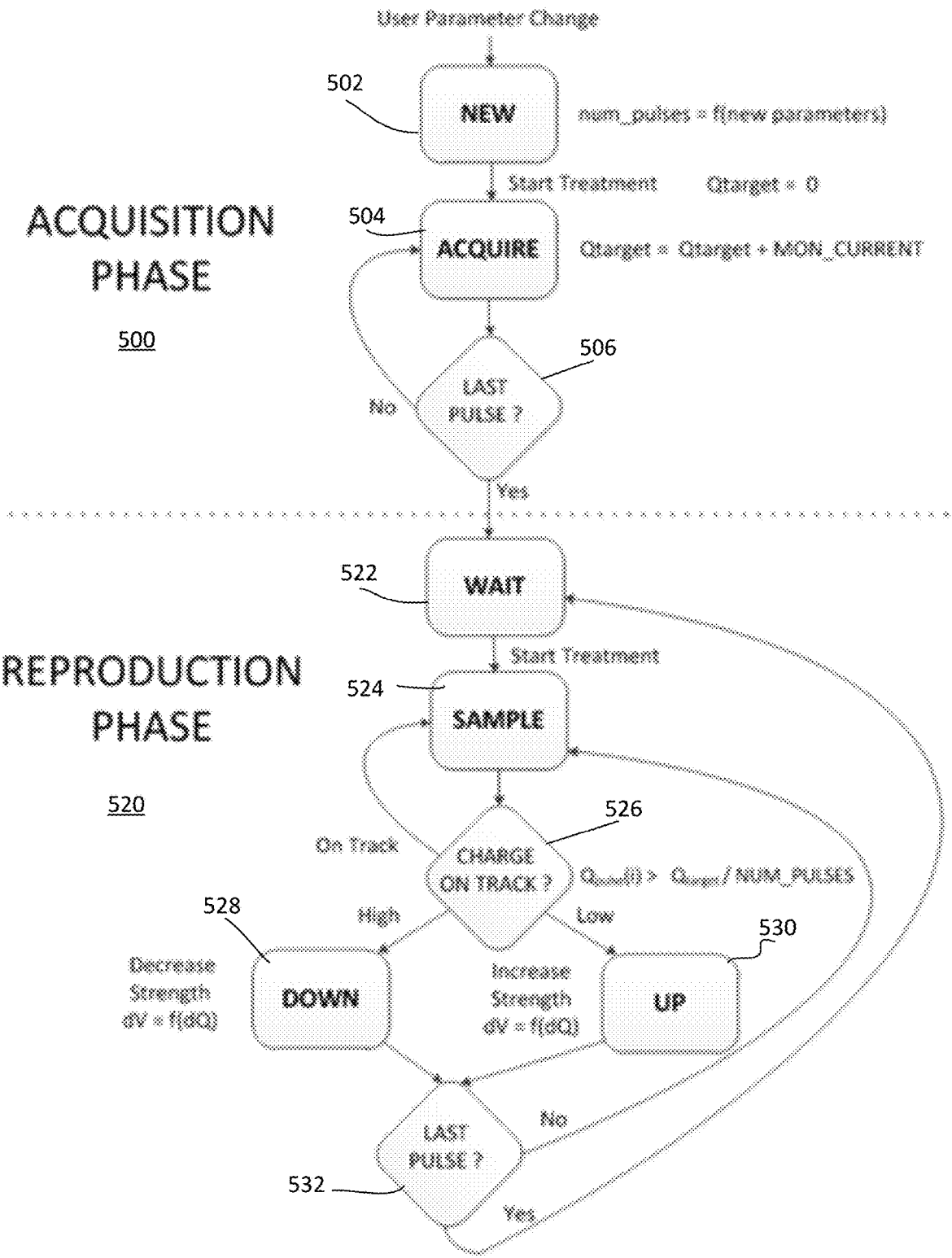
FIG. 5 is a flow diagram in accordance with one example of an adaptive protocol.

A flow diagram in accordance with one example of the adaptive protocol disclosed above is shown in FIG. 5. The adaptive protocol strives to repeatedly and reliably deliver a target charge ("$Q_{target}$") in coulombs during a treatment and to account for any environmental changes. Therefore, the functionality of FIG. 5 is to adjust the charge level applied to a user based on feedback, rather than use a constant level.

The mathematical expression of this protocol is as follows: $Q_{target} = Q_{target}(A*dS + B*dT)$, where A is the Strength Coefficient—determined empirically, dS is the user change in Strength, B is the Duration Coefficient—determined empirically, and dT is the user change in Duration.

Figure 6:
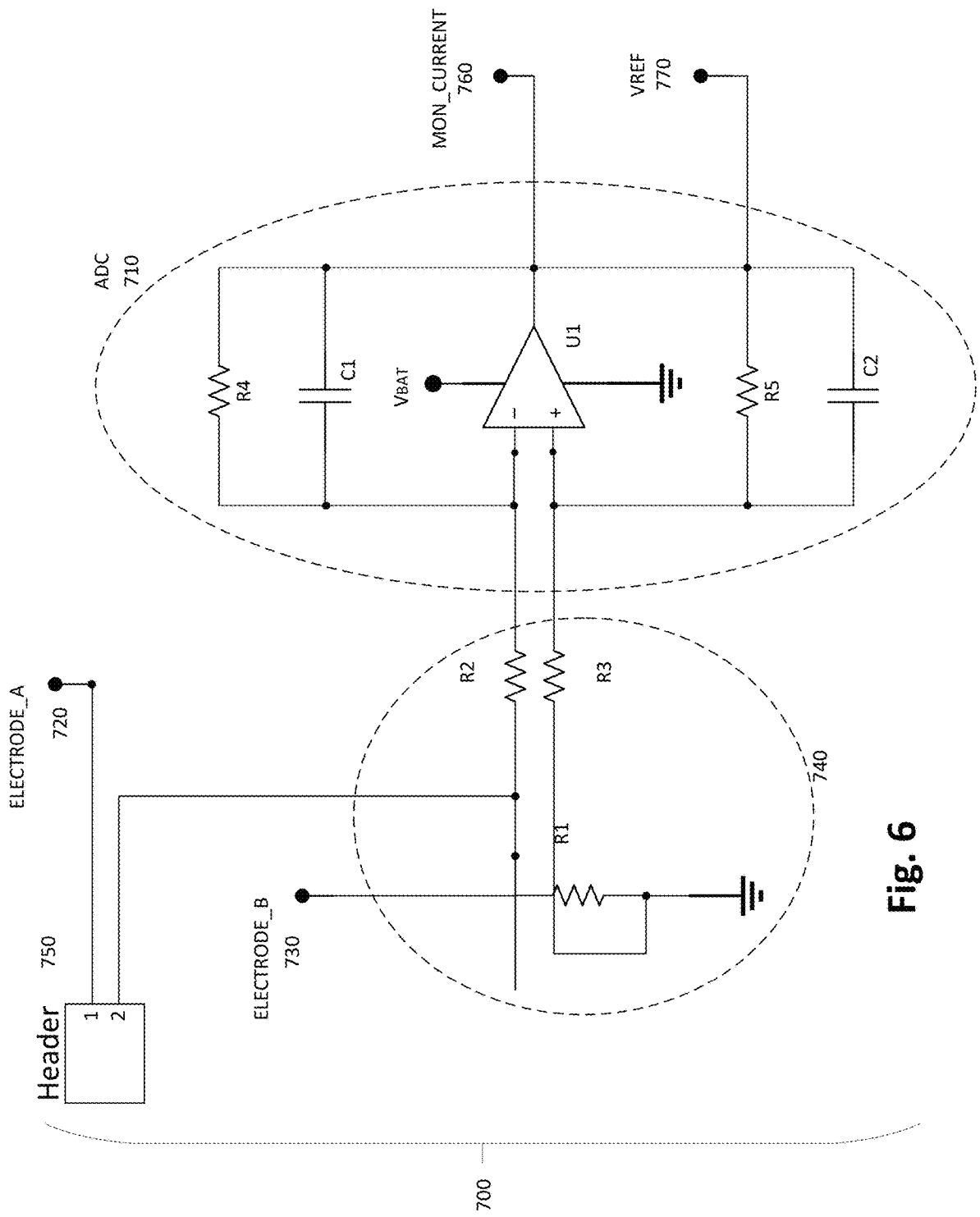
FIG. 6 is a Differential Integrator Circuit used in the adaptive protocol in accordance with one example.

The adaptive protocol includes two phases in one example: Acquisition phase 500 and Reproduction phase 520. Any change in user parameters places the adaptive protocol in the Acquisition phase. When the first treatment is started, a new baseline charge is computed based on the new parameters. At a new acquisition phase at 502, all data from the previous charge application is discarded. In one example, 502 indicates the first time for the current usage where the user places patch 100 on a portion of the body and manually adjusts the charge level, which is a series of charge pulses, until it feels suitable, or any time the charge level is changed, either manually or automatically. The treatment then starts. The mathematical expression of this function of the application of a charge is as follows:

The charge delivered in a treatment is $$Q_{target} = \sum_{i=1}^{T*f} Q_{pulse}(i)$$

Where T is the duration; f is the count of pulses for one treatment (e.g., Hertz or cycles/second) of "Rep Rate"; $Q_{pulse}(i)$ is the measured charge delivered by Pulse (i) in the treatment pulse train provided as a voltage MON_CURRENT that is the result of a Differential Integrator circuit shown in FIG. 6 (i.e., the average amount of charge per pulse). Differential Integrator circuit 700 of FIG. 6 is an example of a circuit used to integrate current measured over time and quantify the delivered charge and therefore determine the charge output over a treatment pulse. The number of pulses in the treatment is T*f.

As shown in of FIG. 6, MON_CURRENT 760 is the result of the Differential Integrator Circuit 700. The Analog to Digital Conversion ("ADC") 710 feature is used to quantify voltage into a number representing the delivered charge. The voltage is measured between Electrode A 720 and Electrode B 730, using a Kelvin Connection 740. Electrode A 720 and Electrode B 730 are connected to a header 750. A reference voltage, VREF 770, is included to keep the measurement in range.

In some examples, Analog to Digital Conversion 710 is an internal feature of controller 270. In some examples, Analog to Digital Conversion 710 is an external component, which delivers its digital output value to a digital input port on Controller 270.

At 504 and 506, every pulse is sampled. In one example, the functionality of 504 and 506 lasts for 10 seconds with a pulse rate of 20 Hz, which can be considered a full treatment cycle. The result of Acquisition phase 500 is the target pulse charge of $Q_{target}$.

FIG. 7 is a table in accordance with one example showing the number of pulses per treatment measured against two parameters, frequency and duration. Frequency is shown on the Y-axis and duration on the X-axis. The adaptive protocol in general performs better when using more pulses. One example uses a minimum of 100 pulses to provide for solid convergence of charge data feedback, although a less number of pulses can be used in other examples. Referring to the FIG. 7, a frequency setting of 20 Hz and duration of 10 seconds produces 200 pulses.

The reproduction phase 520 begins in one example when the user initiates another subsequent treatment after acquisition phase 500 and the resulting acquisition of the baseline charge, $Q_{target}$. For example, a full treatment cycle, as discussed above, may take 10 seconds. After, for example, a two-hour pause as shown at wait period 522, the user may then initiate another treatment. During this phase, the adaptive protocol attempts to deliver $Q_{target}$ for each subsequent treatment. The functionality of reproduction phase 520 is needed because, during the wait period 522, conditions such as the impedance of the user's body due to sweat or air humidity may have changed. The differential integrator is sampled at the end of each Pulse in the Treatment. At that point, the next treatment is started and the differential integrator is sampled for each pulse at 524 for purposes of comparison to the acquisition phase $Q_{target}$. Sampling the pulse includes measuring the output of the pulse in terms of total electric charge. The output of the integrator of FIG. 6 in voltage, referred to as Mon_Current 760, is a direct linear relationship to the delivered charge and provides a reading of how much charge is leaving the device and entering the user. At 526, each single pulse is compared to the charge value determined in Acquisition phase 500 (i.e., the target charge) and the next pulse will be adjusted in the direction of the difference.

$$NUM\_PULSES=(T^*f)$$

After each pulse, the observed charge, $Q_{pulse}(i)$, is compared to the expected charge per pulse.

$$Q_{pulse}(i) > Q_{target}/NUM\_PULSES \ ?$$

The output charge or "$V_{BOOST}$" is then modified at either 528 (decreasing) or 530 (increasing) for the subsequent pulse by:

$$dV(i)=G[Q_{target}/NUM\_PULSES-Q_{pulse}(i)]$$

where G is the Voltage adjustment Coefficient—determined empirically. The process continues until the last pulse at 532.

A safety feature assures that the $V_{BOOST}$ will never be adjusted higher by more than 10%. If more charge is necessary, then the repetition rate or duration can be increased.

In one example a boosted voltage circuit uses dedicated circuits to servo the boosted voltage. These circuits process voltage and/or current measurements to control the PWM duty cycle of the boosted voltage circuit's switch. The system controller can set the voltage by adjusting the gain of the feedback loop in the boosted voltage circuit. This is done with a digital potentiometer or other digital to analog circuit.

In one example, in general, the current is sampled for every pulse during acquisition phase 500 to establish target charge for reproduction. The voltage is then adjusted via a digital potentiometer, herein referred to as "Pot", during reproduction phase 520 to achieve the established target_charge.

The digital Pot is calibrated with the actual voltage at startup. A table is generated with sampled voltage for each wiper value. Tables are also precomputed storing the Pot wiper increment needed for 1 v and 5 v output delta at each pot level. This enables quick reference for voltage adjustments during the reproduction phase. The tables may need periodic recalibration due to battery level.

In one example, during acquisition phase 500, the data set=100 pulses and every pulse is sampled and the average is used as the target_charge for reproduction phase 520. In general, fewer pulses provide a weaker data sample to use as a basis for reproduction phase 520.

In one example, during acquisition phase 500, the maximum data set=1000 pulses. The maximum is used to avoid overflow of 32 bit integers in accumulating the sum of samples. Further, 1000 pulses in one example is a sufficiently large data set and collecting more is likely unnecessary.

After 1000 pulses for the above example, the target_charge is computed. Additional pulses beyond 1000 in the acquisition phase do not contribute to the computation of the target charge. In other examples, the maximum data set is greater than 1000 pulses when longer treatment cycle times are desired.

In one example, the first 3-4 pulses are generally higher than the rest so these are not used in acquisition phase 500. This is also accounted for in reproduction phase 520. Using these too high values can result in target charge being set too high and over stimulating on the subsequent treatments in reproduction phase 520. In other examples, more advanced averaging algorithms could be applied to eliminate high and low values.

In an example, there may be a safety concern about automatically increasing the voltage. For example, if there is poor connection between the device and the user's skin, the voltage may auto-adjust at 530 up to the max. The impedance may then be reduced, for example by the user pressing the device firmly, which may result in a sudden high current. Therefore, in one example, if the sample is 500 mv or more higher than the target, it immediately adjusts to the minimum voltage. This example then remains in reproduction phase 520 and should adjust back to the target current/charge level. In another example, the maximum voltage increase is set for a single treatment (e.g., 10V). More than that is not needed to achieve the established target_charge. In another example, a max is set for $V_{BOOST}$ (e.g., 80V).

In various examples, it is desired to have stability during reproduction phase 520. In one example, this is accomplished by adjusting the voltage by steps. However, a relatively large step adjustment can result in oscillation or over stimulation. Therefore, voltage adjustments may be made in smaller steps. The step size may be based on both the delta between the target and sample current as well as on the actual $V_{BOOST}$ voltage level. This facilitates a quick and stable/smooth convergence to the target charge and uses a more gradual adjustments at lower voltages for more sensitive users.

The following are the conditions that may be evaluated to determine the adjustment step.

delta-mon_current=abs(sample_mon_current−target_charge)

If delta_mon_current>500 mv and $V_{BOOST}$>20V then step=5V for increase adjustments (For decrease adjustments a 500 mv delta triggers emergency decrease to minimum Voltage)

If delta_mon_current>200 mv then step=1V

If delta_mon_current>100 mv and delta_mon_current>5%*sample_mon_current then step=1V In other examples, new treatments are started with voltage lower than target voltage with a voltage buffer of approximately 10%. The impedance is unknown at the treatment start. These examples save the target_voltage in use at the end of a treatment. If the user has not adjusted the strength parameter manually, it starts a new treatment with saved target_voltage with the 10% buffer. This achieves target current quickly with the 10% buffer to avoid possible over stimulation in case impedance has been reduced. This also compensates for the first 3-4 pulses that are generally higher.

As disclosed, examples apply an initial charge level, and then automatically adjust based on feedback of the amount of current being applied. The charge amount can be varied up or down while being applied. Therefore, rather than setting and then applying a fixed voltage level throughout a treatment cycle, implementations of the invention measure the amount of charge that is being input to the user, and adjust accordingly throughout the treatment to maintain a target charge level that is suitable for the current environment.

The Adaptive Circuit described above provides the means to monitor the charge sent through the electrodes to the user's tissue and to adjust the strength and duration of sending charge so as to adapt to changes in the impedance through the electrode-to-skin interface and through the user's tissue such that the field strength at the target nerve is within the bounds needed to overcome the action potential of that nerve at that location and activate a nerve impulse. These changes in impedance may be caused by environmental changes, such as wetness or dryness of the skin or underlying tissue, or by applied lotion or the like; or by tissue changes, such as skin dryness; or by changes in the device's placement on the user's skin, such as by removing the patch and re-applying it in a different location or orientation relative to the target nerve; or by combinations of the above and other factors.

The combined circuits and circuit controls disclose herein generate a charge that is repeated on subsequent uses. The voltage boost conserves battery power by generating voltage on demand. The result is an effective and compact electronics package suitable for mounting on or in a fabric or similar material for adherence to a dermis that allows electrodes to be placed near selected nerves to be activated.

Restless Legs Syndrome System and Treatment

In some example inventions, patch 100, disclosed above, is used for the treatment of RLS and PLM (collectively referred to as "RLS"). The causes of RLS and PLM continue to be under investigation. Studies have shown a correlation between impaired transmission of dopamine signals from the basal ganglia of the brain to the nerves of the muscles. Studies have also shown a hyperactivity in spinal nerves, possibly due to a suppression of normal dopamine-mediated inhibitory signals from the brain to the efferent nerves which control leg movement. Some success for treatment has been shown with medication, such as dopamine agonists, to try to establish normal levels.

The neural system includes many pathways, from the brain, through the spine, to the limbs and the muscles of the limbs. Example inventions are directed to a novel approach for treating RLS by applying electrical stimuli/stimulation ("ES") transcutaneously to leg peripheral nerves (afferent) coming into the spinal dorsal horn and causing a polysynaptic reflex, mediated by one or more interneurons, to inhibit the anterior effector synapses that control the leg muscles. Patch 100, disclosed above, is applied to the dermis in proximity to the nerve to be activated and stimulates one or more of the common fibular nerves and/or branches to achieve the inhibitory effect on the efferent nerves that control leg movement, and thus suppresses RLS.

Example inventions provide an integrated system, including patch 100, which may be placed on the skin of the user and activated and used without the help of a medical professional. Examples include hardware and software to monitor biometrics related to limb movement, and to stimulate one or more nerves to relieve RLS as a closed-loop system. Example inventions eschew implanted stimulation and implanted muscle monitoring in favor of transcutaneous monitoring of muscle movement, and stimulation of the nerves, avoiding any surgical procedures.

Inhibitory actions may be achieved through appropriate afferent stimulations originating from several interconnected nerve pathways in the legs. Stimulation of the common peroneal nerve or the sural nerve which ascends to join the common peroneal nerve may activate inhibitory responses in the spinal column and thus suppress RLS successfully. Other nerves in the lower extremities may also be employed to activate similar inhibitory responses. The implementation of the invention stimulates one or more of these nerves (collectively referred to as the "targeted nerve") to produce inhibition of RLS through the action of inhibitory interneurons existing in the spinal segments.

Figure 8:
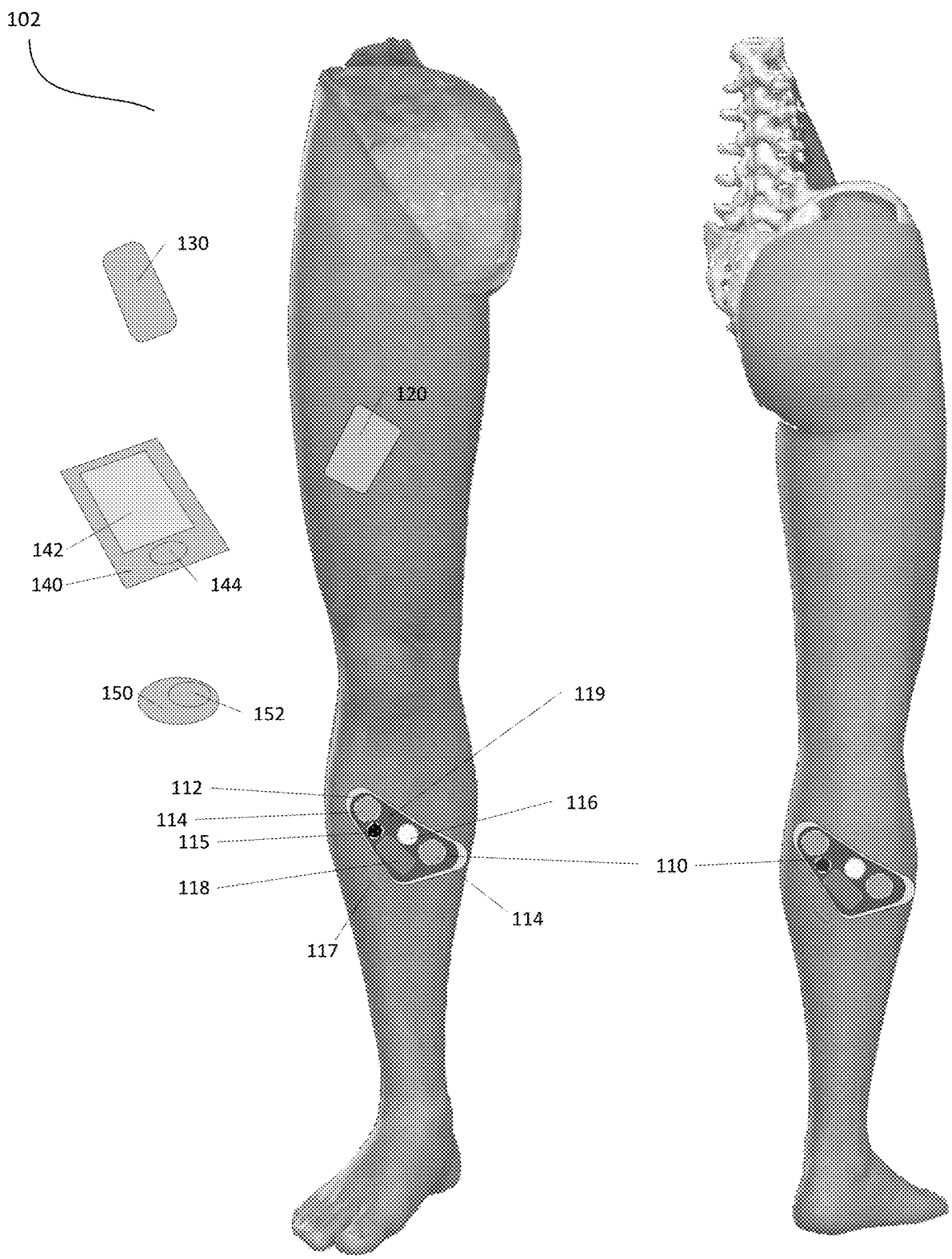
FIG. 8 is an illustration of components of an RLS detection and treatment system 102 in accordance with example inventions.

FIG. 8 is an illustration of components of an RLS detection and treatment system 102 in accordance with example inventions. System 102 includes patch 110 (an example of patch 100 disclosed above), which includes a securing mechanism 112 (e.g., adhesive layer), and one or more electrode pairs 114, with each pair having a positive electrode and a negative electrode (or multiple positive electrodes and a single negative electrode as disclosed below). Patch 110 further includes one or more sensors 115, a power source 116 and a processor 118. System 102 further includes a tag 117, a muscle monitoring device ("MMD") 120 and an optional sleep detection device ("SDD") 130. System 102 further includes an optional smart controller 140 (e.g., a smart phone), with a display 142, and an acknowledgment button 144, and an optional fob 150 with one or more buttons 152.

Figure 9A:
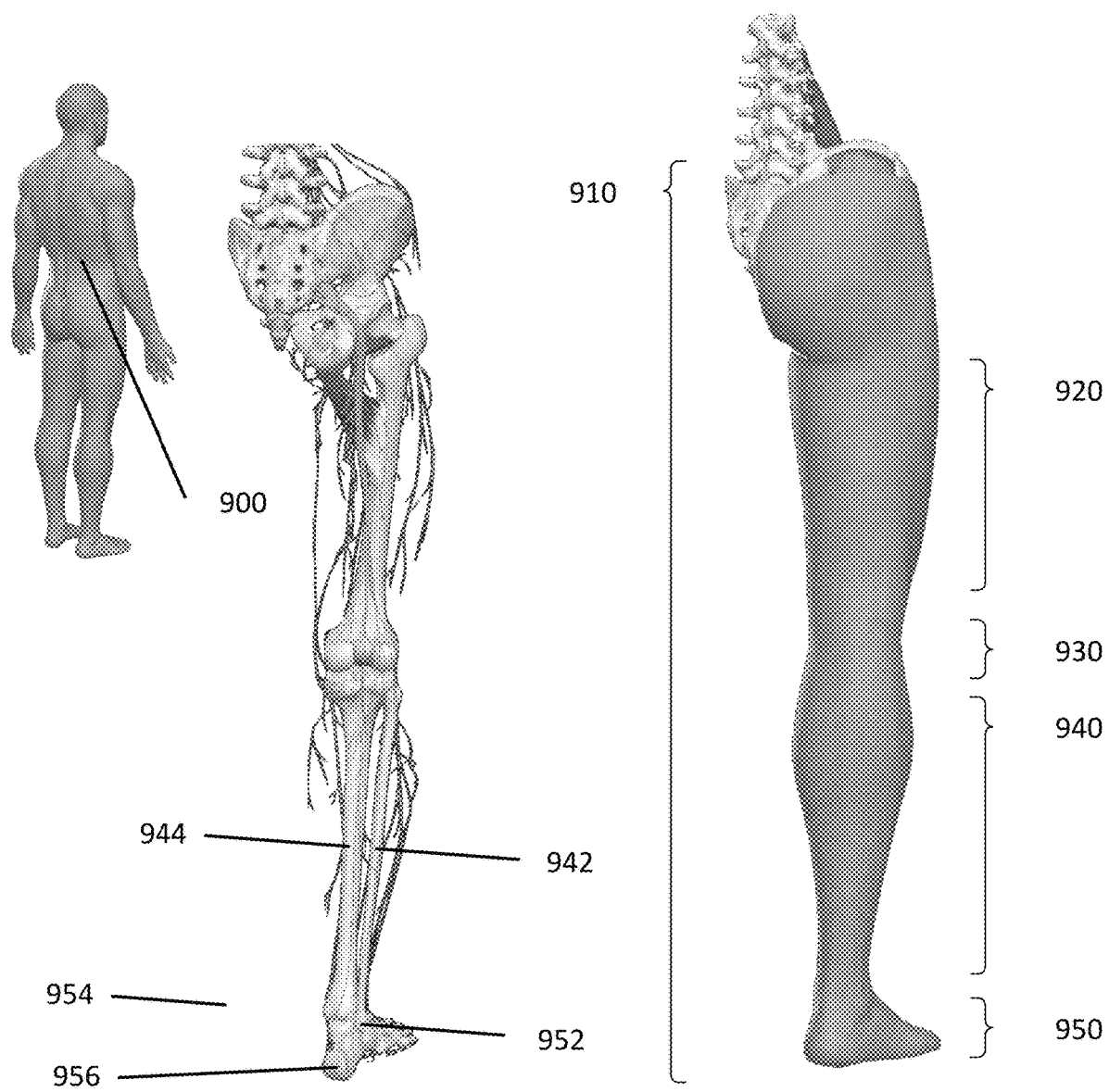
FIGS. 9A and 9B are diagrams of RLS-related nerves and structures.
Figure 9B:
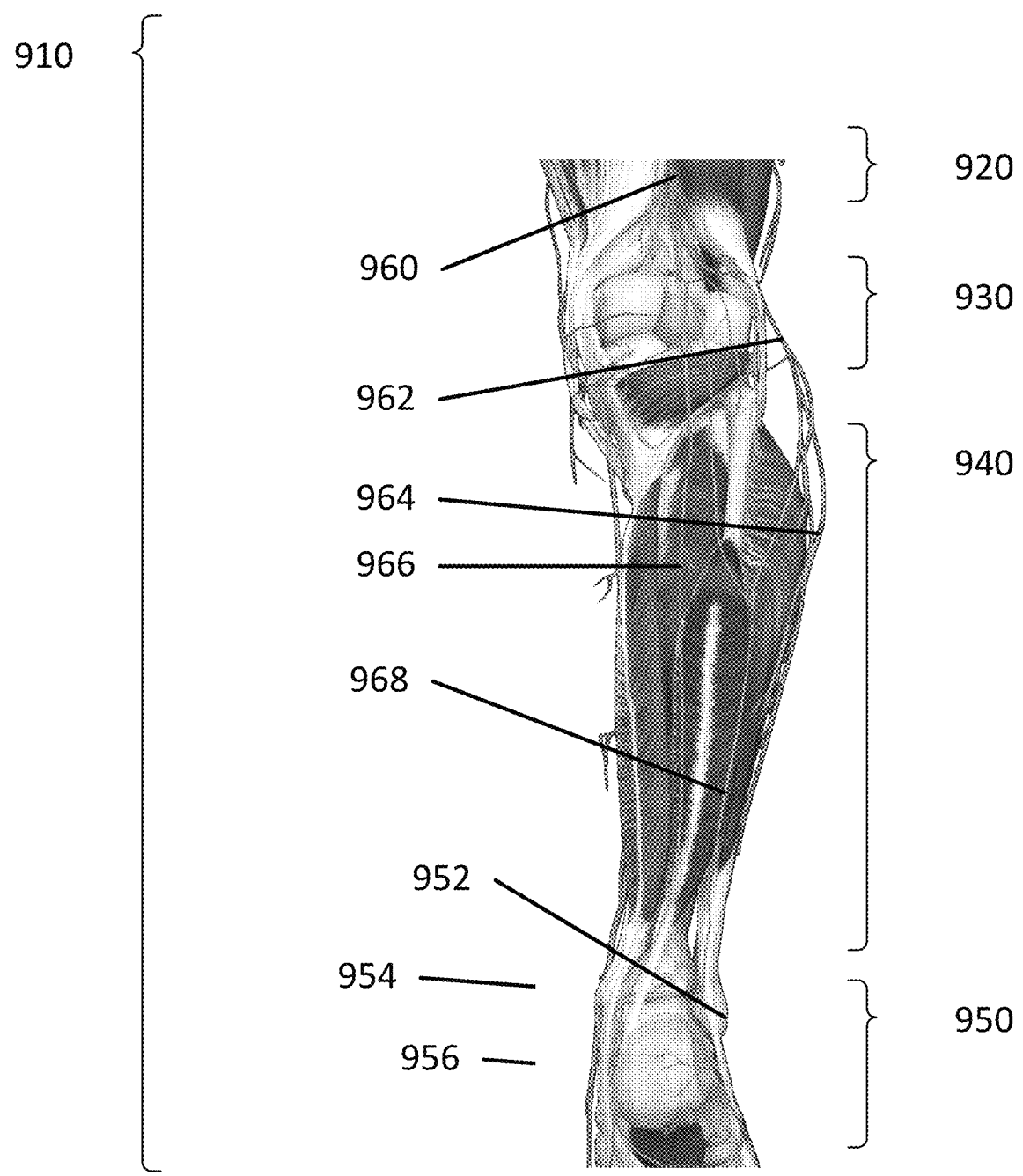

FIGS. 9A and 9B are diagrams of RLS-related nerves and structures. FIG. 9A illustrates details of a leg 910 of a user 900. Leg 910 includes an upper leg 920, a knee 930, and a lower leg 940 that includes a tibia 942 and a fibula 944, and a foot 950 that includes a lateral malleolus 952, a medial malleolus 954 and a heel 956.

FIG. 9B illustrates an internal view of leg 910, including the upper leg 920, the knee 930, and the lower leg 940. Foot 950 includes the lateral malleolus 952, and the heel 956. Leg 910 further includes a sciatic nerve 960, a common peroneal nerve 962 (also referred to as a "common fibular nerve"), and a sural nerve, including a lateral sural nerve 964, and a medial sural nerve 968, the sural nerve ascending to join the common peroneal nerve, and a tibial nerve 966. FIGS. 9A and 9B represent features found on both the left leg and the right leg.

Figure 10:
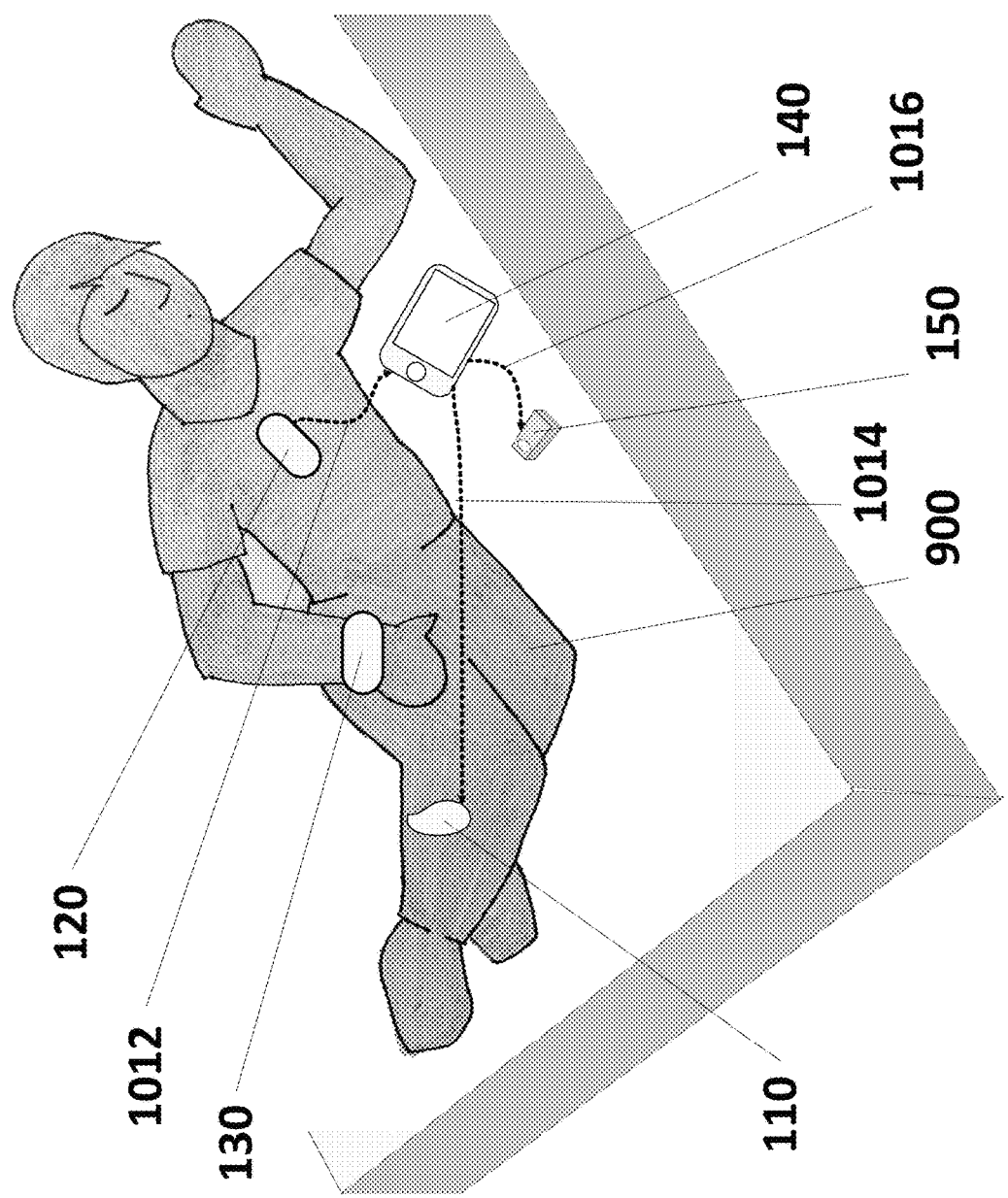
FIG. 10 illustrates the user and the placement of devices in accordance with example inventions.

FIG. 10 illustrates the user 900 and the placement of devices in accordance with example inventions. As shown in FIG. 10, placed on user 900 is patch 110, muscle monitoring device ("MMD") 120, sleep detection device ("SDD") 130, smart controller 140, and fob 150. Also shown are communication paths from SDD-to-smart controller 1012, from smart controller-to-patch 1014, and from smart controller-to-fob 1016. In embodiments, patch 110 is implemented using elements shown in conjunction with patch 100 of FIGS. 1-7 above.

Figure 11:
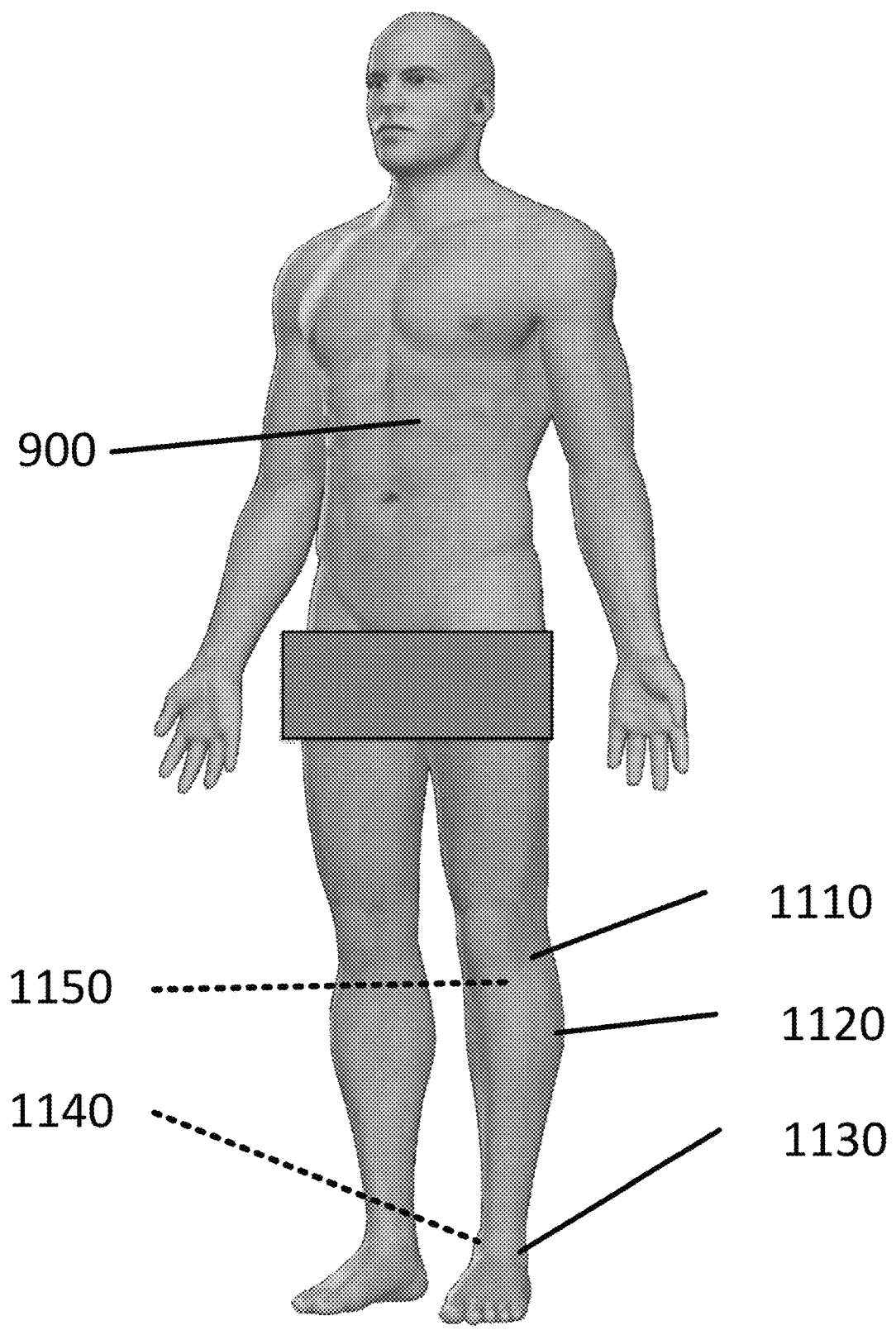
FIG. 11 illustrates example locations on the user at which the patch may be affixed to the skin in accordance to example inventions.

FIG. 11 illustrates example locations on user 900 at which patch 110 may be affixed to the skin in accordance to example inventions. The locations include outside the knee 1110, on the calf 1120, at the lateral side of the ankle 1130, at the medial side of the ankle 1140, and behind the knee 1150. Other points of application are possible as long as they can provide electrical stimuli to the targeted nerves.

In examples, the use of sub-electrodes couples energy efficiently into the target tissues, such as the targeted nerves, while passing effectively through or around other tissues, such as the muscles and the tendons, these tissues being obstructive to electrical energy due to their higher electrical impedances than the impedances of the target Nerves. Patch 110 is designed to be placed on the leg and situated to accurately stimulate the target afferent nerve. In examples, patch 110 placed over the sural nerve or over the fibular nerve.

Figure 12:
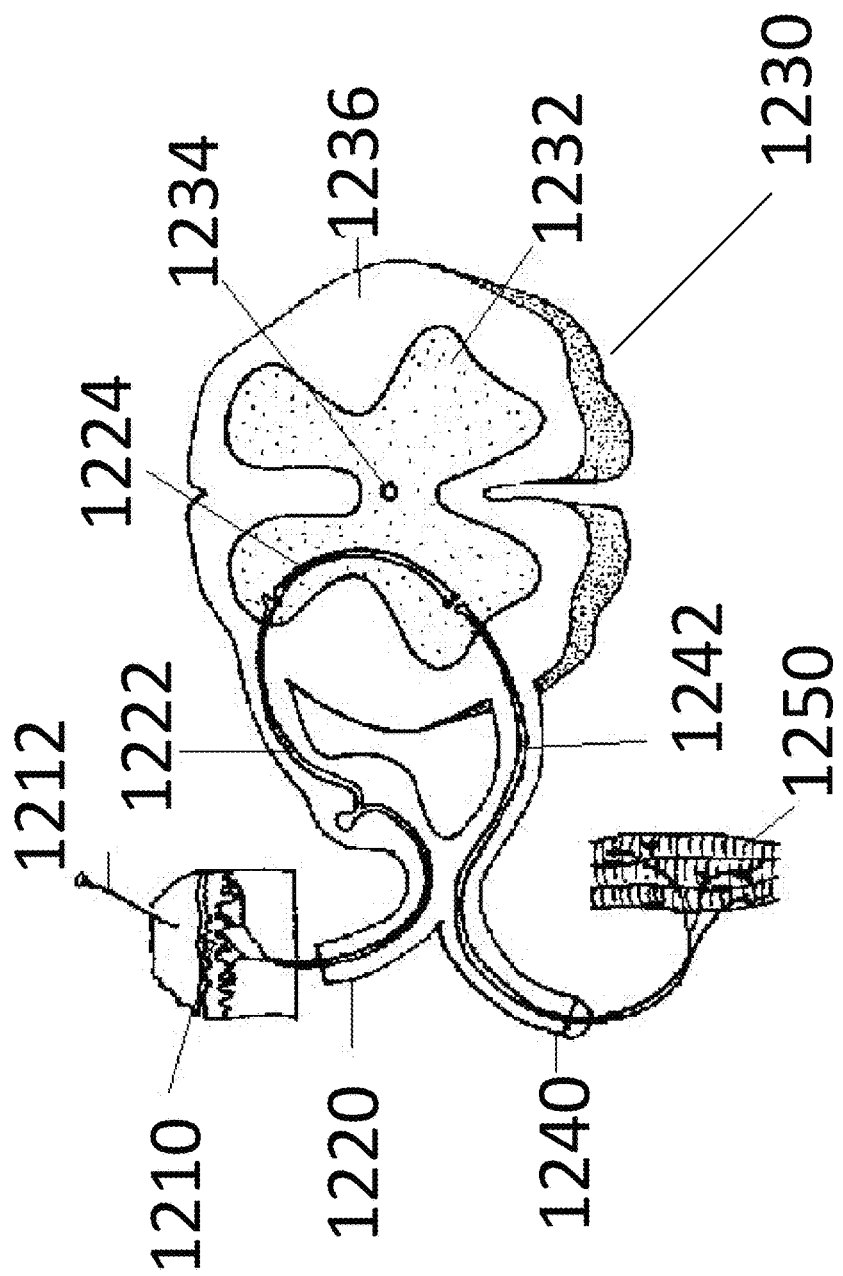
FIG. 12 illustrates a polysynaptic reflex arc that stimulates an afferent nerve.

FIG. 12 illustrates a polysynaptic reflex arc that stimulates an afferent nerve, which in turn activates an inhibitory interneuron which suppresses the activation of an efferent nerve. Sensory nerves 1210 in the skin respond to electrical energy from stimulation 1212. A sensory neuron 1222 travels through a dorsal root 1220 to an interneuron 1224, which is located in the spinal column 1230. The spinal column contains grey matter 1232, white matter 1236, and a central canal 1234. The interneuron transmits its inhibitory nerve impulse to a motor neuron 1242 in a ventral root 1240. The efferent nerve innervates muscle fibers 1250.

Patch 110 is designed in a shape to conform to the skin when affixed to the skin and to be electronically effective at stimulating the common peroneal nerve or the sural nerve in example inventions. Patch 110 may be used for RLS detection, as well as for delivering electrical stimulation. Patch 110 is electronically most effective when the positive and negative electrodes are placed axially along the path of the nerve, in contrast to transversely across the path of the nerve which is not as electronically effective.

The shape of patch 110 in examples is designed to minimize discomfort for the user 900 when affixed in the target location.

In some examples, patch 110 (and all other patches disclosed herein) includes one or more sensors 115 which measure internal features or biometrics of the user in the leg 910 or area near the leg. The measurements are used to help the user to orient and place patch 110 most accurately in the target location and to monitor biometrics related to muscle movement. The sensor data is communicated to one or more of smart controller 140 and fob 150, and is used by patch 110, including an indication such as LED or vibration sent to the user to assist them in placing the device.

In an example, patch 110 includes an electronic sensor 115, in a fixed placement on the patch relative to the electrodes 114. The sensor is used to detect the strength of the activation pulse at the target nerve through the use of a tag 117 previously placed on or near the target nerve. Tag 117 responds to the activation signal from the electrodes to a degree proportional to the strength of the activation signal coupled into the target nerve, and sends this response to patch 110, the strength of this response then used by the user to re-orient or move patch 110 on the leg for optimum performance of the activation on the target nerve.

Figure 13:
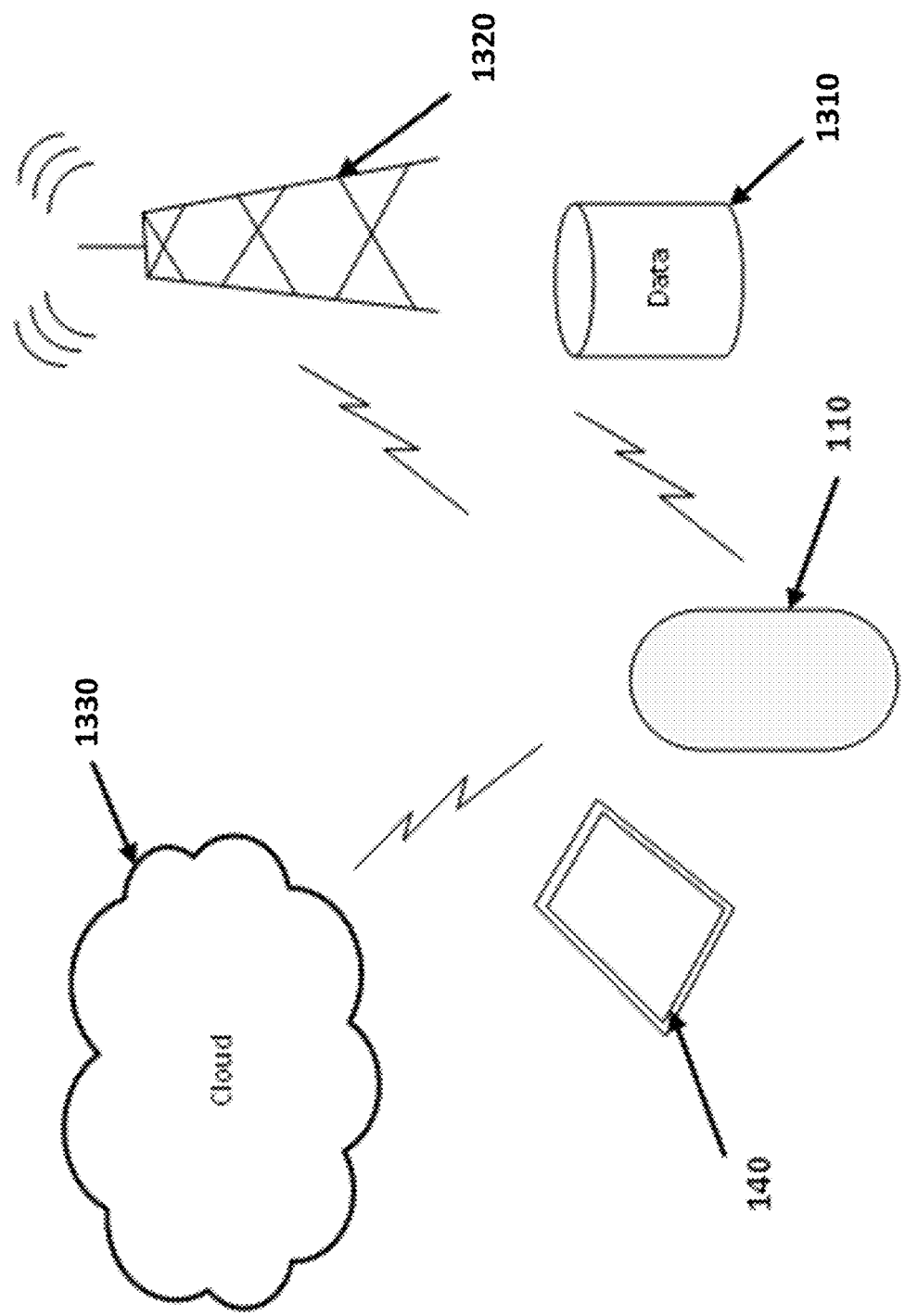
FIG. 13 illustrates the connectivity of the patch and the smart controller with a data store, a network, and the cloud in example inventions.

FIG. 13 illustrates the connectivity of patch 110 and smart controller 140 with a data store 1310, a network 1320, and the cloud 1330 in example inventions.

Figure 14:
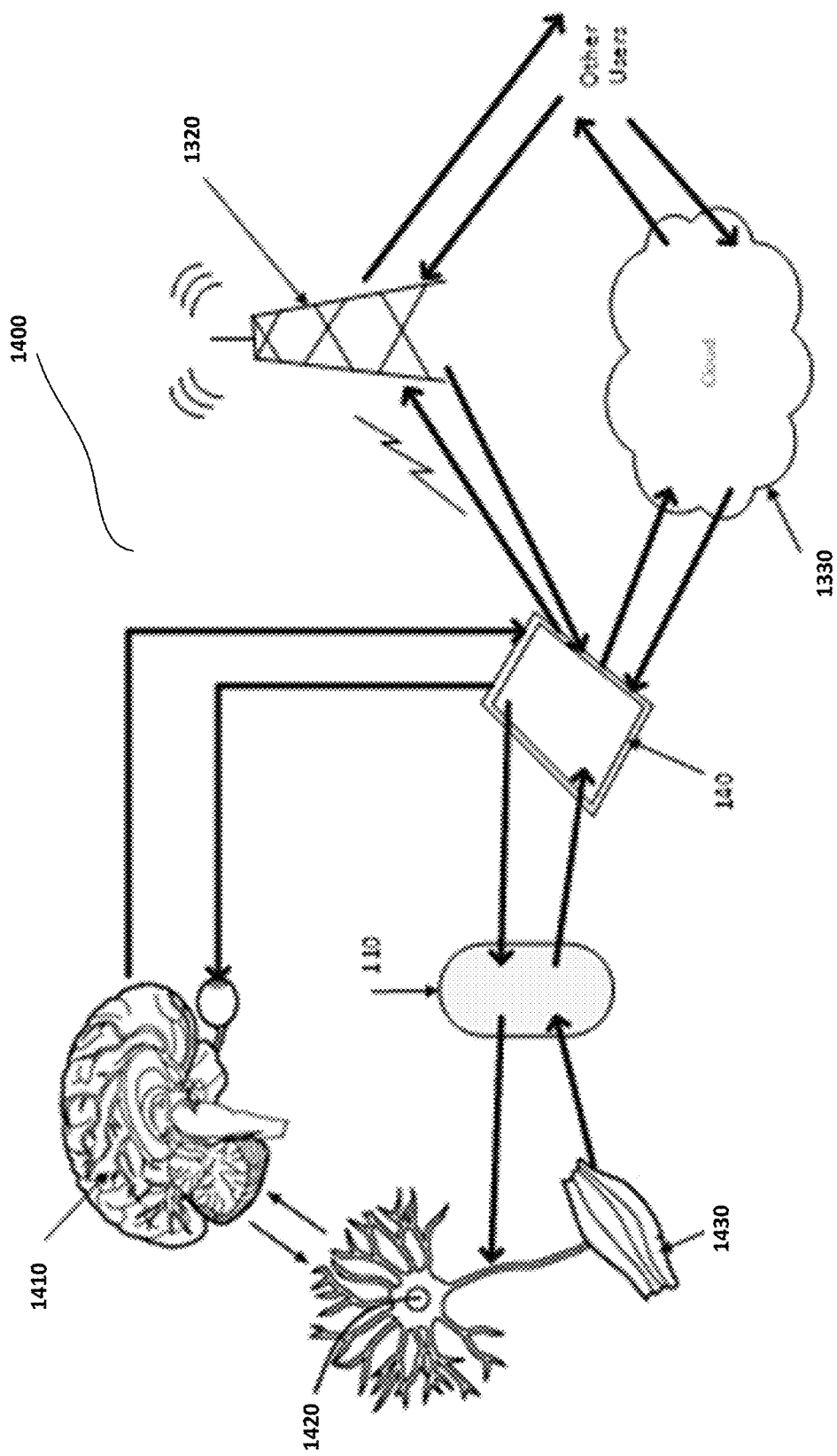
FIG. 14 illustrates a feedback loop to create a closed-loop system between the user, the patch and the smart controller in example inventions.

FIG. 14 illustrates a feedback loop to create a closed-loop system between user 900, patch 110 and smart controller 140 in example inventions.

The sensors of patch 110 may be of several different modalities including pressure sensors, temperature, humidity (sweat), Electromyography ("EMG") sensors, motion, and accelerometers. The sensors can gather biometric data about the user 900 such as the number of steps taken, gait information, contact sequencing of various parts of the foot with the ground, and environmental conditions, such as road surface. The data is gathered by smart controller 140 and/or fob 150, and sent to data store 1310, the network 1320 (e.g., the Internet), or directly to the cloud 1330 via the wireless connection.

In some examples, patch 110 uses one electrode pair 114 to activate the nerve one or more legs. In some examples, patch 110 uses multiple positive electrodes and one or more negative electrodes to activate one or more branches of the nerve, modifying the waveshapes or timings, or both, of the stimulation pulses from the multiple electrodes to direct the waveform energy at one or more specific points on the nerves. Various arrays of electrodes as disclosed above can be controlled to generate optimized stimulation. The stimulation can be adaptive based on feedback from sensors as disclosed above.

The individual components of the RLS detection and treatment system 102 may be connected as peer devices in a Body Area Network, passing each other signals and sharing the tasks of data recording, real-time analysis, and closed-loop monitoring of user 900.

Suppression of RLS

User 900, while awake, but seeking to sleep, experiences the urge to move the leg or legs which provides a distraction or interruption in the process of falling asleep. User 900 can signal to patch 110 using smart controller 140 or fob 150 such that patch 110 initiates a stimulation of the target afferent nerve to suppress the symptoms of RLS.

In one example, user 900 enables patch 110 to stimulate using a repeating protocol for a period of time set by the user. The period of time is started by the user, and continues for a period sufficient to allow the user to fall asleep and avoid symptoms of RLS.

In one example, smart controller 140 or fob 150 or both start a repeating protocol for a period of time set by analysis of data collected from previous periods of attempting to fall asleep. This data may be collected from the individual user to characterize their sleep pattern, or from a population of people, deducing through machine learning or artificial intelligence a pattern of falling asleep to define the period of stimulation.

Detection Using Muscle Monitoring Device

The function of MMD 120 is to detect occurrences of muscle movement due to RLS, and to notify one or more of patch 110, smart controller 140 or fob 150 of such an episode. MMD 120 includes of one or more accelerometers. The accelerometer detects sporadic movements of muscles, or the lack of such movement.

For example, user 900 may enable MMD 120 using one or both of smart controller 140 or fob 150 when the user seeks to fall asleep. MMD 120 monitors leg movements while the user is immobile and seeking to sleep and reacts to movement to signal to patch 110 to stimulate the target afferent nerve. The user disables the MMD when seeking to stay awake, such as in the morning after sleeping, such that the MMD stops monitoring leg movements.

Sleep Detection Device

User 900 experiences symptoms of RLS while asleep, such as movement of one or both legs. In many cases, these movements are not consciously detected by the user, but the movements affect the quality of sleep.

SDD 130 may be positioned at various locations on the body, depending upon which sensor and which body parameters are measured. For example, an SDD including an accelerometer may be positioned on the chest to detect rhythmic breathing patterns or on the neck in the submental region, or on the lower neck at the suprasternal notch. An SDD including a CO2 sensor or an audio sensor may be positioned near the outside of the nasal passageway.

The function of the optional SDD 130, worn by the user, is to detect changes in the user's body position as the position relates to sleeping or not sleeping, such as standing, or sitting, or prone, using one or more sensors, such as accelerometers. SDD 130 further notifies one or more of patch 110, smart controller 140 or fob 150 of such position change, thereby indicating the start or end of a sleep period, or interruption to sleep.

The specification of a sleep period may also be determined by other signals such as time of day, location of the user, amount of activity, posture, and other signals.

In one example, user 900 indicates explicitly their position as prone versus non-prone on smart controller 140 through the use of the display 142 or the acknowledgment button 144, or with fob 150, or other means. When smart controller 140 is informed of the user's prone position, such as when resting but not sleeping, smart controller 140 places patch 110 and MMD 120 into a state of monitoring RLS episodes. When smart controller 140 is informed of the user's position as not related to RLS, such as standing or walking, smart controller 140 places patch 110 and MMD 120 into a state of standby, no longer monitoring RLS episodes.

In an example, when user 900 indicates explicitly their position to smart controller 140, SDD 130 is not used, or the decision of SDD 130 is overridden by the user's explicit input, such as when intending to lie prone but not sleep.

In an example, smart controller 140 determines the prone position of user 900 without the use of the SDD 130, such as through the use of a GPS, an accelerometer and other sensors attached to the user or separate from the user such as in the bed, analyzing data from these features internal to smart controller 140. For example, the location of smart controller 140 or fob 150, or both, at the bedside or in the bed for longer than a pre-set time limit may be used as an indicator that the user is in the bed and in a prone and sleeping position.

In an example, user 900 is prompted by and indicates to smart controller 140 the locations in which the user sleeps, such as a bed in a bedroom, such that the data on locations collected in this manner by smart controller 140 allows smart controller 140 to determine when the user is in those new locations at a later time, such as when visiting another home or traveling.

SDD 130 may be a separate unit from patch 110, and may be positioned at various anatomical locations around the body away from patch 110, or may be integrated within patch 110, and may monitor specific body signals at the same location as patch 110.

In an example, SDD 130 may send data related to sleep to smart controller 140 during the user's sleep period while the patch stimulation function is not activated, this data being collected to determine if the user exhibits signs of RLS.

In one example, smart controller 140 or fob 150, or both, is in control of a sleep partner or medical service provider such as a sleep researcher. When MMD 120 detects an event, a notification is sent to smart controller 140 or fob 150, and a second person may record the RLS event.

In one example, the second person may activate patch 110 based upon visual and auditory clues arising from user 900. The second person may also observe the effects of stimulation upon the user, and record reactions, either electronically in smart controller 140 or fob 150, or manually such as in a diary.

In one example, the second person may monitor and respond to the signals from multiple users' RLS detection and treatment systems 102, or from a database of historical recordings of the user's sleep and wake patterns, or a database of a large population of anonymized user sleep and wake recordings that have been analyzed with pattern recognition or AI techniques including machine learning and deep learning techniques.

In one example, RLS detection and treatment systems 102 may use electrocardiogram ("ECG"), or encephalogram ("EEG"), electromyogram ("EMG"), or other means to detect muscles in an RLS event; and to detect the user in the state of rapid eye movement ("REM") sleep, or in non-REM sleep. The system may then apply RLS treatments in a manner appropriate to each type of sleep or wakefulness.

Patch 110, smart controller 140, and fob 150 may be combined in a variety of ways to implement RLS detection and treatment system 102. In some examples, user 900 uses fob 150 to send data and controls to smart controller 140. In some examples, user 900 uses fob 150 to send data and controls to patch 110. In some examples, user 900 uses smart controller 140 directly, and a fob 150 is not used.

In some examples, fob 150 communicates data and controls with smart controller 140 or to patch 110, or both, through wireless means, through the use of Bluetooth Low Energy ("BLE"), Wi-Fi, or other means.

In some examples, power source 116, smart controller 140, and fob 150 may be powered by battery or rechargeable means.

Smart controller 140 may also communicate information to other users, experts, or application programs via network 1320 or via the cloud 1330, and receive information from them via network 1320 or via the cloud 1330.

The user 900 may choose to initiate or modify these processes, sometimes using protocol applications residing in patch 110, smart controller 140, or the network 320, such as the Internet or wireless networks. This software may assist the user, for example, by processing the stimulation to be delivered to the body to render it more selective or effective for the user, and/or by processing and displaying data received from the body or from network 1320 to make it more intelligible or useful to the user.

Data Collection

In an example, analysis of measurements from one or more of smart controller 120, MMD 120 and SDD 130 may be performed by processing in a remote server, in the cloud, or on a computer separate from the smart controller but local to the user, such as a personal computer.

In an example, RLS detection and treatment system 102 measures the user's RLS events over a period of days or weeks or longer, noting the clock time when the user begins an RLS event and the clock time when the user ends an RLS event. The system analyzes this data and determines the most effective clock times to activate RLS detection and treatment system 102.

In an example, RLS detection and treatment system 102 collects time-based records of a user's RLS events. These records are entered into a database of anonymized RLS period information from large populations of RLS detection and treatment system 102 users, or with recordings of RLS periods from other detection systems.

In an example, RLS detection and treatment system 102 uses AI techniques such as pattern recognition and correlation analysis to correlate real-time data recordings of the user with larger population databases to produce comparative or predictive analyses. An example, machine-learning algorithms are employed to build up the user's RLS history and provide specific predictors of RLS severity and associated conditions.

In an example, the time-based records of RLS periods are supplemented with data entered manually by one or more observer of the user's RLS events. The data recorded in the time-based database is sent to the cloud through a local network, such as a home mesh network, or directly over the Internet.

RLS Treatment

Figure 15:
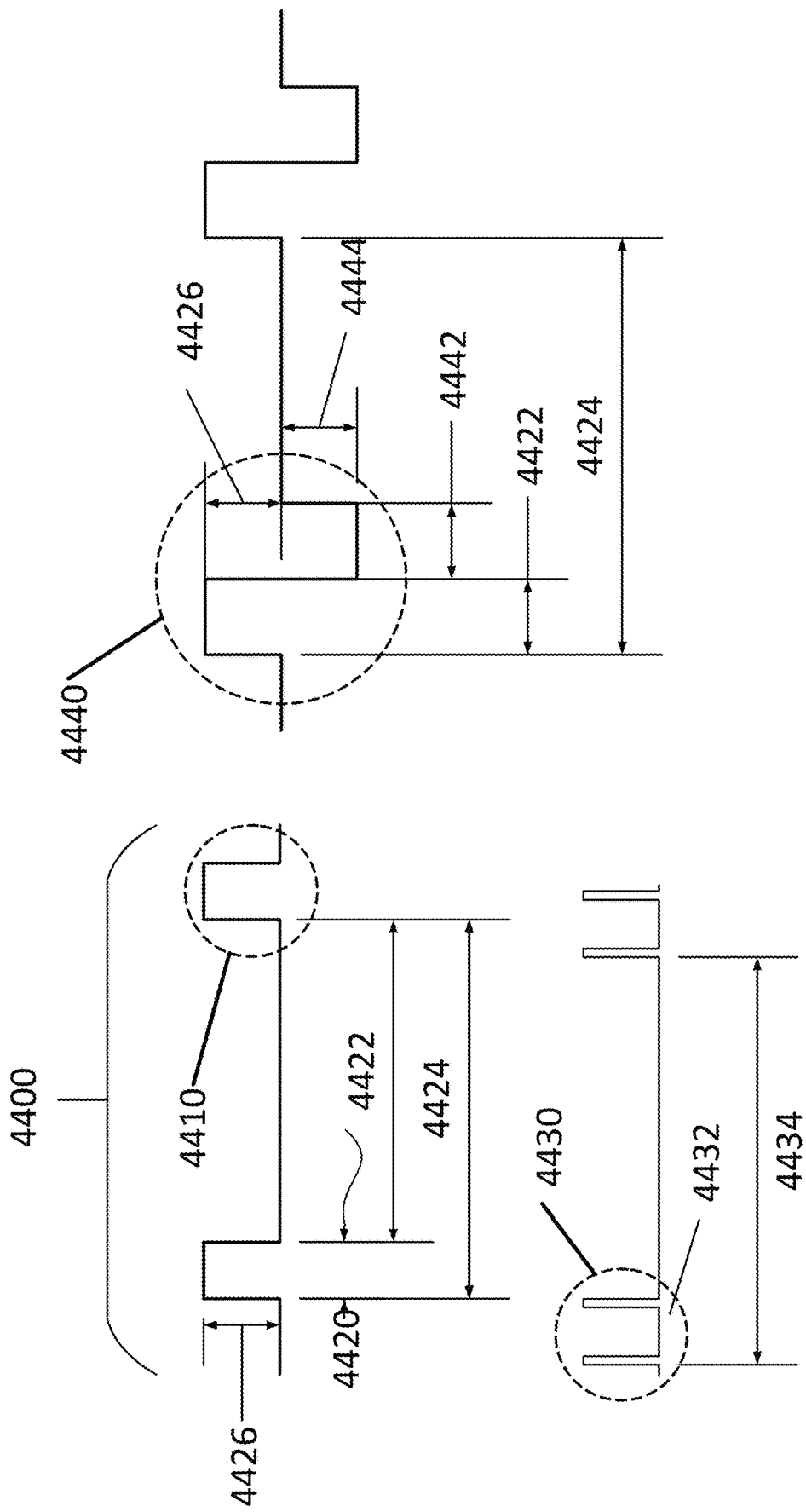
FIG. 15 illustrates example stimulation waveforms for treating RLS in accordance with example inventions.

FIG. 15 illustrates example stimulation waveforms for treating RLS in accordance with example inventions. Patch 110 stimulates the one or more targeted nerves using a series of electrical pulses in a pattern of pulse sequence 4400 with a specific frequency, waveform, intensity and duration. Pulses 4410 are applied at an intensity below that level which stimulates a painful sensation and below that level which wakes user 900.

In examples, each pulse has a pulse high time 4420, a pulse low time 4422, a pulse period 4424, and a pulse amplitude 4426. Pulses 4410 may be monopolar pulses or bipolar pulses 4440. For monopolar pulses, the pulse period 4424 is the sum of the pulse high time 4420 and the pulse low time 4422. Bipolar pulses have a negative pulse width 4442 and a negative pulse amplitude 4444, for the purpose of balancing the DC bias of the sequence of stimulation pulses, and for the purpose of balancing for zero net energy into the tissues. The negative pulse width may differ from the pulse high time. The negative pulse amplitude may differ from the pulse amplitude. Pulse shapes are affected by the impedance coupling to the user's tissues and by the patch 3010 output impedance, internal drive strength, and other factors, such that the pulses, whether monopolar or bipolar, may not be square waves.

One or more of the pulse high time 4420, the pulse low time 4422, the pulse period 4424, and the pulse amplitude 4426 may be adjusted. For bipolar pulses 4440, the negative pulse width 4442 and negative pulse amplitude 4444 may be adjusted from one user to another user, or from one application of a device to another on the same user. The pulse pattern may be adjusted during the course of a treatment.

Pulses may be output in bursts 4430. Each burst has two or more pulses 4410, or bipolar pulses 4440. Each burst has a burst pulse count 4432 and a burst period 4434. One or both of the burst pulse count and the burst period are adjustable for each user, or from one application of a device to another on the same user. The pulse frequency is the inverse of the pulse period. The burst frequency is the inverse of the burst period.

Pulses or bursts may be adjusted by each user each time a patch 110 is applied, since effective intensity may be different according to skin condition, dampness, dryness, weight change, specific location of placement and other factors. In this manner, the electrical pattern of stimulation pulses is adjusted for each application/treatment.

As an example, the applied frequency of the stimulation pulses 4410 may be in the range of 2 Hz to 50 Hz, and the current applied may be up to 10 milliamps. Further, pulses 4410 singly or in bursts 4430 may have pulse high times 4420 in the range of 100 to 500 microseconds, and pulse low times 4422 in the range of 100 to 500 microseconds, with burst frequency and pulse frequency for single pulses in the range of 2 Hz to 50 Hz, and the current applied is in the range 0.1-10 mA.

In examples, the pulses within one burst may all be of equal width. In examples, the pulses within one burst may be of varying widths, the width adjusted to optimize the stimulation for effectiveness.

In examples, the pulses within one burst may be evenly spaced. In examples, the pulses within one burst may be unevenly spaced. In examples, the pulses within one burst may have consistent amplitude. In examples, the pulses within one burst may have unequal amplitudes.

As such, the intensity of the applied pulses is adjusted for each user and may be adjusted and applied by each user each time patch 110 (or any other patches disclosed herein) is applied, since effective intensity may be different according to skin condition, dampness, dryness, weight change, specific location of placement and other factors. In this manner, the electrical pattern of stimulation pulses is adjusted for each application.

As an example, processor 118 adjusts the intensity of applied pulses, or the duration of application, or both, using data from the monitoring device or devices, such as MMD 120, included in RLS detection and treatment system 102.

As another example, smart controller 140 adjusts the intensity of applied pulses, or the duration of application, or both, using data exchanged with patch 110 and its processor. The exchanged data includes data from the monitoring device or devices included in RLS detection and treatment system 102.

As another example, one or both of patch 110 and smart controller 140 adjusts the intensity or the duration of the applied pulses, or both, and user 900 adjusts the intensity and the duration of the applied pulses, or both, with all adjustments limited to preset ranges.

In an example, one or more of the intensity, the pulse high time, the pulse low time, the pulse count per burst, and the burst count are adjusted by one or more of patch 110, smart controller 140 and user 900.

In an example, one or more of pulse rise time, pulse fall time, pulse overshoot, and pulse undershoot are adjusted by one or both of patch 110 and smart controller 140. Changes in pulse shape, including one or more of rise time, fall time, overshoot and undershoot, allow the patch to optimize use of power during the application of a treatment protocol. Optimizing the power used in a treatment allows a patch with a given design to apply more stimulation when compared to a patch without the means to optimize power delivery. Pulse shape is limited by one or both of patch and smart controller such that delivered energy, rate of energy delivery, magnitude of currents and/or voltages all meet the requirements for effective nerve stimulation at the applied position.

In an example, one or both of patch 110 and smart controller 140 operate to select one of a variety of hardware configurations, each hardware configuration on the patch specified to limit one or more of pulse rise time, pulse fall time, pulse overshoot, and pulse undershoot. One example uses a bank of capacitors, switched into the pulse application circuit under control of the patch, to optimize the load and its effect on the driven pulse voltage and current. A second example uses a bank of inductive loads. A third example uses a bank of resistive loads.

In an example, patch 110 is applied to the skin from 1 to 5 centimeters below the user's knee 930.

In an example, patch 110 is designed in a shape to appear as a shape of equal size on the left and right sides on the midline when properly affixed to the skin, so that the electrical stimulation is effective through the tissue.

In an example, patch 110 is designed in a shape to appear as a shape with unequal size on the left and right sides on the midline when properly affixed to the skin, the underlying design of In an example, patch 110 arranging the electrode pairs 114 so that the stimulation is effective through the tissue.

The placement of patch 110 onto leg 910 may be difficult for some users due to the angle of view to that part of their anatomy. For some users, aligning the device to one or more specific anatomical features, such as the center of the kneecap, may provide sufficient guidance to properly position the device. For some users, additional prompts may be required.

In an example, a separate device, such as a smart phone or camera, is mounted on a surface or held by user 900 or held by a second person, and provides a view of the target area for patch 110 such that the user or a second person may accurately place patch 110 on the skin. In an example, a separate device, such as a smart phone or goggles, uses augmented reality features to display for user 900 certain additional images or markers in relation to one or both of the target location on the user and the real time location of patch 110 before affixing it to the user, such that these additional images or markers, or both, are used to assist the user in accurate placement at the target location.

In an example, a mark or indicator on patch 110 is used by user 900 to align the device properly on leg 910. As an example, a template is provided to user 900, including markings or indicators on the template to simplify positioning of the template in the prescribed position on the leg. The template is used to provide a marked location for proper positioning of patch 110. The template is removed from the skin after proper placing of patch 110.

In an example, the template is disposable and used one time by user 900. In an example, the template is reusable and saved by user 900 for repeated use in aligning and positioning patch 110 on leg 910. As an example, patch 110 initiates a low-intensity stimulation intended to trigger a perceptible sensation in the user if and only if the device is properly positioned on the skin. This sensation may be a muscle twitch, a tingling, or similar, which provides no purpose except as a confirmation of positioning. The user may, after affixing the device to the skin and feeling no sensation, pull the device off of the skin and reposition it, repeating this process until the sensation is felt and the device is properly positioned.

As an example, processor 118 adjusts the intensity of applied pulses, or the duration of application, or both, using data from the monitoring device or devices, such as MMD 120, included in the RLS detection and treatment system 102. As an example, smart controller 140 adjusts the intensity of applied pulses, or the duration of application, or both, using data exchanged with patch 110 and its processor 118. The exchanged data includes data from the monitoring device or devices included in RLS detection and treatment system 102.

In an example, one or both of patch 110 and smart controller 140 adjusts the intensity or the duration of the applied pulses, or both. User 900 adjusts the intensity and the duration of the applied pulses, or both and all adjustments can be limited to preset ranges. In an example, one or more of the pulse intensity, the pulse high time, the pulse low time, the pulse count per burst, the burst count are adjusted by one or more of patch 110, smart controller 140 and user 900.

Electrode Arrangements

In examples, patch 110 (including any other patches disclosed herein) can use multiple positive electrodes in an array or matrix and also include multiple negative electrodes. Each positive electrode creates an electric field with the negative electrode nearest to it, such that the charge flows from one electrode to the other. Each positive electrode's field is not affected by other negative or positive electrodes, as these other electrodes are electrically distant from the positive electrode and the negative electrode. However, this set of electrodes may complicate the physical and electrical layout of the patch.

Therefore, in example inventions, a set of positive electrodes instead shares only one common negative electrode, such that the return current path back to the stimulating circuit is through the one negative electrode. This common negative electrode is larger than individual negative electrodes for each positive electrode when considering the two approaches on a fixed patch area. By making the common negative electrode larger, its impedance can be lower to the skin, its fringe area is minimized such that uncomfortable stimulation sensations are minimized when compared to current paths through small electrodes, and leakage currents are minimized because the single, larger negative electrode may be more easily isolated from circuitry than a multiplicity of negative electrodes.

The set of positive electrodes may be connected to the stimulating circuit one at a time or more than one at a time, using low-impedance switches between the shared voltage generating stimulation circuit and the individual electrodes. The switches are controlled by the controller, such that only the desired positive electrode or electrodes are connected at one time.

The patch may use one positive electrode and a set of negative electrodes. The positive electrode is driven by the voltage for stimulation, using one circuit and working through the lower impedance of the large, common positive electrode in its contact with the skin. The negative electrodes may be a common ground, and connected to each other by conductive paths on the patch and further back to the stimulating circuit to complete the current loop. Alternatively, each negative electrode may be connected to the common ground through a low-impedance switch, the switches being under control of the controller, such that only the desired negative electrode or electrodes are connected to ground at one time, thereby limiting the return current path.

The set of positive electrodes driven by a stimulation voltage may have individually adjusted stimulation voltages such that, when connected and stimulating the skin, the combined stimulation from multiple positive electrodes is more effective than identical stimulation waveforms from all positive electrodes. The currents from each of the positive electrodes passes through the common negative electrode and back to the stimulating circuit. Individual stimulating waveforms are created by individual stimulating circuits which have specific setups under control of the controller. The controller may adjust the amplitude, phase, pulse width, and frequency of each circuit to create a combination of stimulation through multiple positive electrodes.

In general, when patch 110 is applied to the skin and then uses sensors to detect when to stimulate, it uses sensing circuits that are separate from the circuits used for electrical stimulation. When the detection mechanism involves electrical signal sensing, the sensors use electrodes on the skin-facing surface of the patch. The controller monitors certain conditions through electrical signal sensing, then turns electrical stimulation on or off according to the treatment regime associated with the sensed condition. For example, muscle twitching may be detected by electromyography ("EMG"). Patches use separate sensing electrodes and stimulation electrodes since each as different requirements.

However, separate sensing and stimulating electrodes increases the size of the patch and may require accurate placement of the patch. In contrast, in some examples, patch 100 uses the same set of electrodes for sensing as for stimulating. The connections to the controller are shared between sensing and stimulating functions, or the connection to each electrode is routed to unique controller pins with a low-impedance switch. The state of the switch is controlled by the controller, multiplexing sensing and stimulating functions.

Sensing requires a relatively high-impedance path from the skin surface to the analog-to-digital converter ("ADC") circuit. The ADC may be a discrete component, passing a digital signal on to the controller, or the ADC may be integrated in the controller on one or more pins. High-impedance is required to generate a voltage proportional to the biometric, such as in EMG, the voltage having a range large enough to discriminate a wide set of values when digitized.

Stimulation requires a relatively low-impedance path to the skin surface, such that the driving circuit can overcome the impedance and drive energy into the tissue for treatment.

The two competing requirements may be combined through the use of a low-impedance or matched-impedance switch. The switch routes the signal captured at the electrode to either the sensing pin or the driving pin. For example, a single pin on the controller may be programmable to low- or high-impedance, and be able to both sense and drive into its load.

In another example, a small part of a larger stimulating electrode may be electrically isolated in the layout such that the small part may work as a sensing electrode when connected to the sensing circuit, and yet may work as part of the overall stimulating electrode when connected to the stimulating circuit. The isolation may be through two switches, one with low impedance for the sensing function, the other with impedance matching the overall impedance of the larger electrode. This latter aspect helps to minimize reflections and aberrations in the stimulating waveform when the stimulating circuit drives both the larger electrode area and the connected smaller area.

In another example, a patch uses a set of small electrodes to stimulate the skin. The overall impedance of the stimulating patches in combination is low, to optimize the effectiveness of the stimulation. The impedance of each individual small electrode is higher, such that it is effectively used in a sensing circuit.

Figure 16:
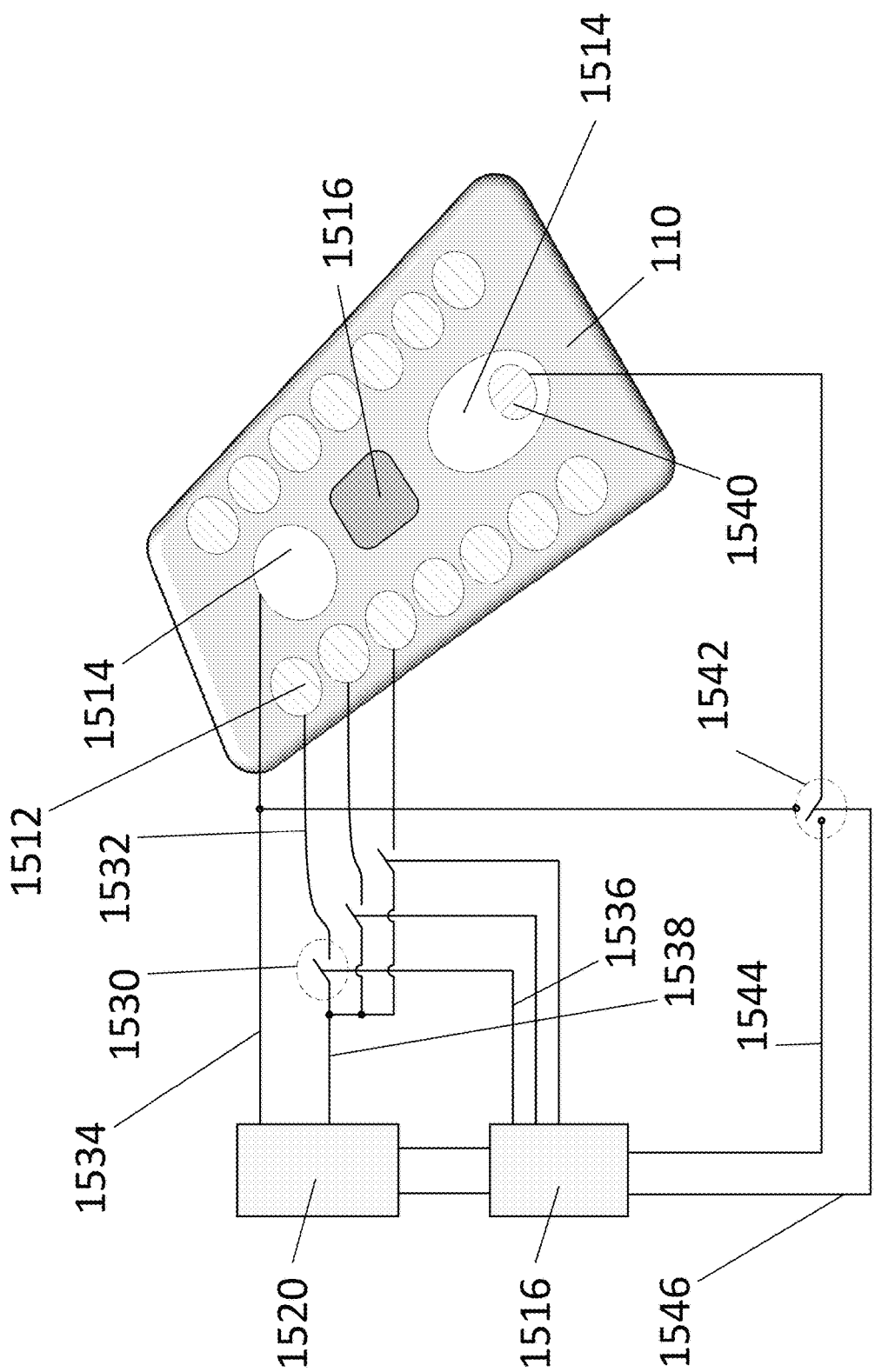
FIG. 16 illustrates the patch with multiple electrodes that are adapted to provide both stimulation and sensing in accordance with example inventions.

FIG. 16 illustrates patch 110 with multiple electrodes that are adapted to provide both stimulation and sensing in accordance with example inventions. Patch 100 includes a set of 14 positive electrodes 1512; and a set of 2 negative electrodes 1514. Patch 110 further includes a processor 1516 shown in a physical view and schematic view. Patch 100 further includes a stimulation voltage circuit 1520, a set of stimulation switches 1530 with a stimulation voltage wire 1532 and a return current wire 1534. Patch further includes a stimulation switch control wire 1536, and a sensor electrode 1540 with a sensing wire 1544, a sensing mode switch 1542, and a sensing mode wire 1546. FIG. 15 illustrates only 3 of the necessary 14 stimulation switches and associated wires that would be included in this example invention.

In operation, patch 110 selects one or more of positive electrodes 1512, connecting each to stimulation voltage circuit 1520 with the corresponding stimulation switch 1530. The stimulation voltage passes from stimulation voltage circuit 1520 to all of the selected positive electrodes 1512, then as a field to negative electrodes 1514, and back to stimulation voltage circuit 1520. In example inventions, patch 100 selects the subset of the available positive electrodes 1512 to optimize the stimulation of the underlying tissue. The selection is adjusted in the software or firmware of processor 1516 according to the positioning of patch 110 on or near the target area.

Further, in example inventions, patch 110 selects the one or more sensor electrodes 1540 by activating sensing mode switch 1542 to connect the sensor to processor 1516. Processor 1516 uses one or more of hardware or software or firmware to analyze the measurement procured from sensor electrode 1540, using the analyzed measurement to inform the selection of positive electrodes 1512. Patch 110 changes the mode of sensing mode switch 1542 to connect sensor electrode 1540, or to return current wire 1534 when the electrode is used during a stimulation.

Data Manager

In examples, patch 100 includes a data manager implemented by control unit/processor 1002, that has primary responsibility for the storage and movement of data to and from the communications controller, sensors, actuators, and a master control program. The data manager has the capability to analyze and correlate any of the data under its control. It provides logic to select and activate nerves. Examples of such operations upon the data include: statistical analysis and trend identification; machine learning algorithms; signature analysis and pattern recognition, correlations among the data within a data warehouse, a therapy library, tissue models, electrode placement models, and other operations. There are several components to the data that is under its control as disclosed below.

The data warehouse is where incoming data is stored; examples of this data can be real-time measurements from the sensors, data streams from the Internet, or control and instructional data from various sources. The data manager will analyze data that is held in the data warehouse and cause actions, including the export of data, under master control program control. Certain decision making processes implemented by the data manager will identify data patterns both in time, frequency, and spatial domains and store them as signatures for reference by other programs. Techniques such as EMG, or multi-electrode EMG, gather a large amount of data that is the sum of hundreds to thousands of individual motor units and the typical procedure is to perform complex decomposition analysis on the total signal to attempt to tease out individual motor units and their behavior. The data manager will perform big data analysis over the total signal and recognize patterns that relate to specific actions or even individual nerves or motor units. This analysis can be performed over data gathered in time from an individual, or over a population of patch users.

The therapy library contains various control regimens for patch 100. Regimens specify the parameters and patterns of pulses to be applied by patch 100. The width and amplitude of individual pulses may be specified to stimulate nerve axons of a particular size selectively without stimulating nerve axons of other sizes. The frequency of pulses applied may be specified to modulate some reflexes selectively without modulating other reflexes. There are preset regimens that may be loaded from the cloud or 3rd party apps. The regimens may be static read-only as well as adaptive with read-write capabilities so they can be modified in real-time responding to control signals or feedback signals or software updates. One such example of a regimen has parameters A=40 volts, t=500 microseconds, T=1 Millisecond, n=100 pulses per group, and f=20 per second. Other examples of regimens will vary the parameters within ranges previously specified.

The tissue models are specific to the electrical properties of particular body locations where patch 100 may be placed. Electric fields for production of action potentials will be affected by the different electrical properties of the various tissues that they encounter. The tissue models are combined with regimens from the therapy library and the electrode placement models to produce desired actions. Tissue models may be developed by MRI, Ultrasound or other imaging or measurement of tissue of a body or particular part of a body. This may be accomplished for a particular user and/or based upon a body norm. One such example of a desired action is the use of a tissue model together with a particular electrode placement model to determine how to focus the electric field from electrodes on the surface of the body on a specific deep location corresponding to the nerve in order to stimulate the nerve selectively to reduce incontinence of urine, or to treat RLS. Other examples of desired actions may occur when a tissue model in combination with regimens from the therapy library and electrode placement models produce an electric field that stimulates targeted nerves.

Electrode placement models specify electrode configurations that patch 100 may apply and activate in particular locations of the body. For example, patch 100 may have multiple electrodes and the electrode placement model specifies where these electrodes should be placed on the body and which of these electrodes should be active in order to stimulate a specific structure selectively without stimulating other structures, or to focus an electric field on a deep structure. An example of an electrode configuration is a 4 by 4 set of electrodes within a larger array of multiple electrodes, such as an 8 by 8 array. This 4 by 4 set of electrodes may be specified anywhere within the larger array such as the upper right corner of the 8 by 8 array. Other examples of electrode configurations may be circular electrodes that may even include concentric circular electrodes. Patch 100 may contain a wide range of multiple electrodes of which the electrode placement models will specify which subset will be activated. Electrode placement models complement the regimens in the therapy library and the tissue models and are used together with these other data components to control the electric fields and their interactions with nerves, muscles, tissues and other organs. Other examples may include patch 100 having merely one or two electrodes, such as but not limited to those utilizing a closed circuit.

Stack-Up of the Patch

Figure 17:
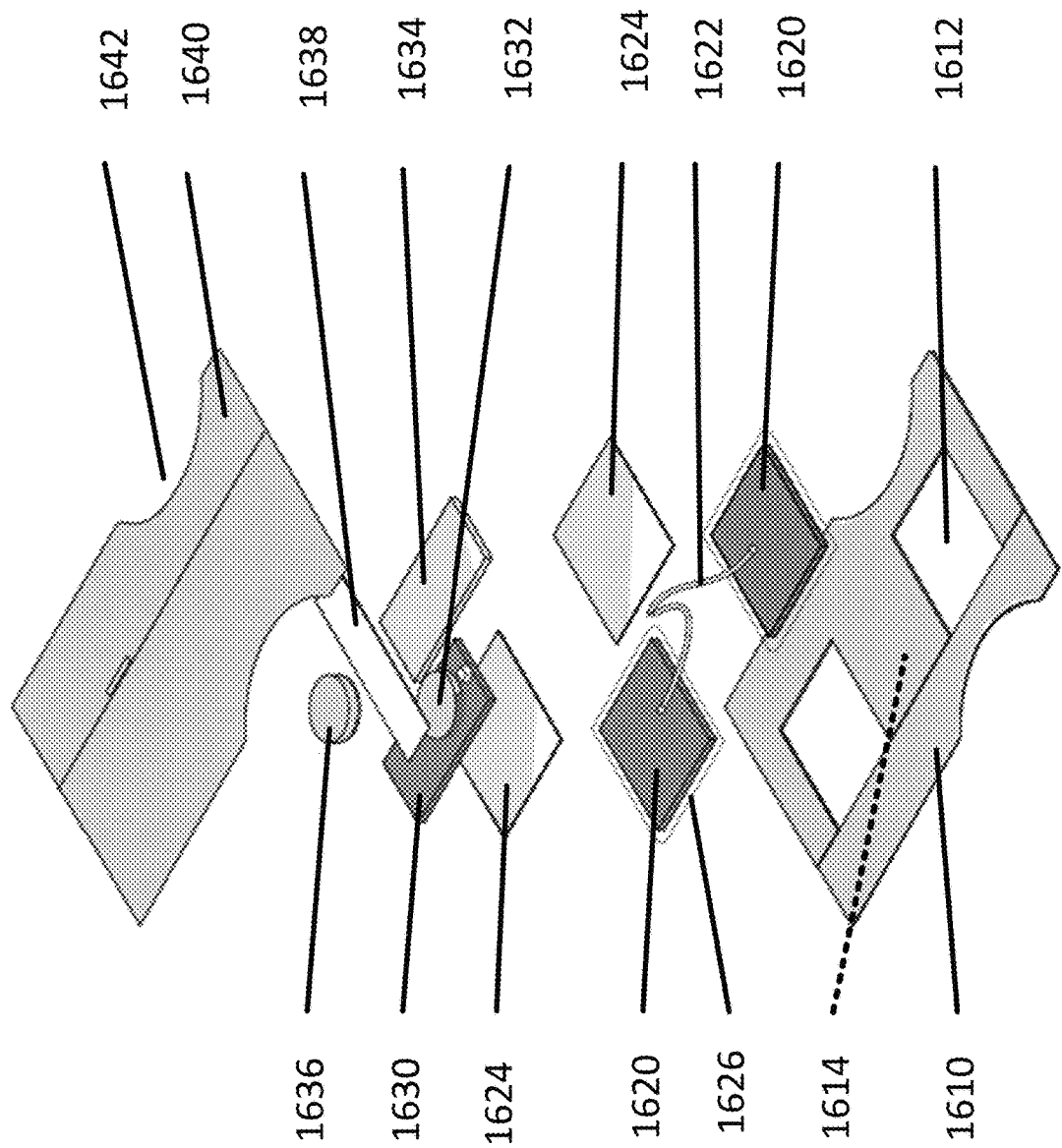
FIG. 17 illustrates a stack-up view of the patch accordance to example inventions.

FIG. 17 illustrates a stack-up view of patch 110 in accordance with example inventions. A bottom layer 1610 is a fabric tape with adhesive on the skin-facing side. A hole 1612 is cut into the bottom layer for each of the electrodes 1620. A removable paper 1614 adheres to the adhesive on the skin-facing side of bottom layer 1610. Two or more electrodes 1620 are coupled by a wire 1622 to a printed circuit board assembly ("PCBA") 1630.

Electrodes 1620 are covered with a polyimide tape A 1624 to prevent short circuits from electrodes 1620 to PCBA 1630 and to prevent movement of electrodes 1630 within the layers of the assembly. Each electrode 1630 is coated on the skin-facing surface with hydrogel 1626. Each electrode 1620 has a release layer covering hydrogel 1626. A battery clip 1632 is attached to PCBA 1630. A battery 1636 is inserted into battery clip 1632. A battery pull tab 1638 is inserted into battery clip 1632. PCBA 1630 is wrapped in polyimide tape B 1634 to restrict access by the user to the electronics. A top layer 1640 of fabric tape with adhesive on the PCBA-facing side is stacked on top to complete the assembly. Ankle bone cutouts 1642 are designed into the shapes of bottom layer 1610 and top layer 1640 to accommodate the ankle bone and to assist the user to correctly place patch 100.

Hydrogel Adaptation

Variations in the viscosity and composition of hydrogel 1626 leads to variation in the migration of the substance from its original area on each electrode to a wider area, possibly touching the skin outside the dimensions of patch 100. As the hydrogel migrates, its electrical performance changes. The circuitry on PCBA 1630 measures the voltage applied to the skin in real-time during the course of each treatment. The adaptive circuit calculates the charge delivered to the skin, which is a function of many parameters, including the conductivity of hydrogel 1626. Therefore, the performance of patch 100 is maintained while the hydrogel portion of the device changes its performance. The adaptive circuit adjusts the delivery of charge to also account for all changes in body and skin conductivity, perspiration and patch contact.

As the performance of the hydrogel 1626 decreases with time, the adaptive circuit and the firmware in PCBA 1630 records the expected life of the specific patch while it is powered on and on the skin of the user. When patch 100 determines that the device's lifetime is near an end, the firmware signals to the fob or smart controller, such that the user receives an indication that this patch has reached its limit.

Crimped Connection from Electrode to PCBA

Each electrode 1620 is coated with hydrogel 1626 when the electrode is manufactured. In some examples, a wire 1622 is connected to both the electrode and the PCBA 1630 in a permanent fashion, such as by soldering, when electrodes 1620 are manufactured. The electrode-plus-wire-plus-PCBA assemblies are each enclosed in an airtight bag until they are subsequently assembled with the tapes and adhesive layers to form a complete patch 100. Due to the complex nature of these assembly steps, the hydrogel on the electrodes may be exposed to air and humidity for a period of time which affects the life expectancy of the hydrogel.

In an example, electrodes 1620 are coated with hydrogel 1626 but no wire is attached at that stage. Instead, a small clip is soldered to each electrode which does not affect the hydrogel nor attach the electrode to any larger assembly which would require longer time in the assembly line. These coated electrodes are each encased in an airtight bag with a heat seal or other means. The hydrogel does not degrade during the time that the coated electrode is inside the sealed bag.

In an example, wire 1622 is inserted into the small clip which had previously been soldered to electrode 1620, this connection being stronger and less prone to defect than the soldering or attachment of the wire strands directly to electrode 1620. The clip and the wire do not affect hydrogel 1626. Each coated electrode 1620, with its clip and attached wire, is encased in an airtight bag with a heat seal or other means. Hydrogel 1626 does not degrade during the time that the coated electrode is inside the sealed bag. The coated electrodes 1620 are removed from their airtight bags only immediately before they are connected to PCBA 1630.

An additional benefit of separating the coated electrodes 1620 from PCBA 1630 as two different subassemblies until put into a completed patch 100 is that coated electrodes found to be defective or expired from too lengthy time on the shelf may be discarded without the expense of discarding an already-attached PCBA. The more expensive PCBAs have a shelf life independent of the shelf life of the coated electrodes. These two subassemblies' inventories may be stocked, inspected and managed independently. This reduces the overall cost of manufacture of patches 100 devices without affecting their performance.

Die Cut Fabric Tape

In some examples, bottom layer 1610 is placed as a layer over electrodes 1620 using a solid layer of fabric tape. The overall thickness of patch 100 is therefore partly determined by the thickness of the fabric tape over electrodes 1620. Further, in order to place electrodes 1620 on the layer of fabric tape securely, the paper cover on the fabric tape must be pulled back to expose the adhesive coating. This results in a degradation of the adhesive properties of the tape.

In examples of patch 100, bottom layer 1610 fabric tape is cut to create holes 1612 for each of electrodes 1620, according to the defined sizes of those components. Each electrode 1620 is placed in the corresponding hole, without the added thickness of a fabric tape layer on top. Since no paper cover needs to be pulled back to mount electrodes 1620 to the fabric tape, the adhesive of the fabric tape is not affected. The holes may be cut with a die in order to create accurate edges, without tears or fibers which may interfere with electrodes 1620.

Contoured to Ankle Bone

In some examples, patch 100 has a rectangular shape. This allows PCBA 1630, battery 1636 and electrodes 1620 to fit in between fabric and adhesive bottom layer 1610 and top layer 1640, and to be affixed to the skin by the user, then to be peeled away and discarded after use. In some examples, patch 100 has a shape contoured to the position in which it is to be affixed to the skin. The reference point in properly positioning patch 100 is the malleolus, or ankle bone in some example uses. Therefore, patch 100 has an ankle bone cutout 1642 along the vertical side, this cutout accommodating the ankle bone when patch 100 is placed close alongside the ankle bone.

In some examples, cutout 1642 is designed into patch 100 on only one side, such that battery 1636, PCBA 1630 and electrodes 1620 are properly aligned on one of the left or the right ankle. Patch 100 can then be offered in two varieties—one for the left ankle with cutout 1642 on the first vertical side, and one for the right ankle with cutout 1642 on the second vertical side.

In some examples, cutout 1642 is designed into patch 100 on both vertical sides, such that battery 1636, PCBA 1630 and electrodes 1620 are properly aligned on either of the left or right ankle. Patch 100 can then be offered in only one variety.

Battery and Battery Tab

Patch 100 includes battery 1636, which is enclosed by battery clip 1632, assembled onto PCBA 1630. During manufacturing, battery 1636 is inserted into battery clip 1632 to secure it from dropping out. In addition to the battery itself, battery pull tab 1638 is placed between one contact of battery 1636 and the corresponding contact in battery clip 1632. Battery pull tab 1638 prevents electrical connection between battery 1636 and battery clip 1632 at that contact until battery pull tab 1638 is removed. When in place, there is an open circuit such that patch 100 is not activated and does not consume power until battery pull tab 1638 is removed.

In some examples, battery pull tab 1638 is designed to be removed by pulling it out in the direction opposite that in which battery 1636 was inserted into battery clip 1632. This pulling action may lead to movement of the battery itself since it experiences a pulling force toward the open side of battery clip 1632. This battery movement may cause patch 100 to cease operating or to never activate.

In one example, battery pull tab 1638 and battery clip 1632 are designed so that battery pull tab 1638 is pulled out in the same direction as battery 1636 was pushed into battery clip 1632. Therefore, the force pulling battery pull tab 1638 out of patch 100 serves only to make battery 1636 more secure in its battery clip 1632. This reduces the chance of inadvertent movement of battery 1636 and the effect on activation or operation of patch 100.

Electrode Release Film

Each of electrodes 1620 in the assembled patch 100 is covered with a Polyethylene Terephthalate ("PET") silicon covered release film 1626. The release film is pulled away by the user when patch 100 is affixed to the skin. In some examples, the PET silicon covered release film 1626 is transparent. This may lead to instances of confusion on the part of the user when the user may not be able to determine if the tape has been removed or not. Affixing patch 100 to the skin with any of electrodes 1620 still covered with tape will cause patch 100 to be ineffective. This ineffectiveness may not be noticed until the first treatment with patch 100. If the affixed patch 100 is found to be ineffective when the user is feeling an urge to urinate, the user may struggle to either properly void their bladder or to remove patch 100, peel off the tapes from the electrodes or affix a new patch 100 and suppress the urge with the re-affixed or new device.

In examples, PET silicon covered release film 1626 covering electrodes 1620 is selected in a color conspicuous to the user, such that the user will readily determine if the tape has been removed or not.

Examples use circuitry and firmware to stimulate the electrode circuit with a brief, low energy pulse or pulse sequence when patch 100 is initially activated. If patch 100 is activated before it is affixed to the skin, the electrode readiness test will fail. In such a case, the electrode readiness test is repeated, again and again according to timers in the firmware or hardware, until either the timers have all expired or the test passes. The test passes when patch 100 is found to exhibit a circuit performance appropriate to its design. The test fails when patch 100 is not properly prepared, such as not removing the electrode films, or is not yet applied to the skin when the timers have all expired. When the electrode readiness test fails, patch 100 signals to the fob or the smart controller, which in turn informs the user. The electrode readiness test is implemented in a manner which may be undetectable by the user, and to minimize the test's use of battery power.

Removable Paper

In some examples, a removable paper 1614 covers the adhesive side of bottom layer 1610. Removable paper 1614 may be in multiple sections, each to be pulled away by the user when affixing patch 100 to the skin. These removable papers may be in addition to the piece of PET film 1626 covering each electrode 1620. Therefore, the user must remove all of these pieces to expose a complete, adhesive surface to affix to the skin in examples.

In examples, bottom layer 1610 is one complete piece, with one removable paper 1614. The user removes all of the removable paper in one motion. In examples, bottom layer 1610 is two or more pieces, with two or more removable papers 1614. The user removes all of the removable papers. In examples, the single removable paper 1614 is designed with a pull tab, so that the user pulls the removable paper off of the bottom layer in a direction at right angle to the long axis of patch 100. This motion reduces the forces experienced by the assembled internal components of patch 100.

In examples, removable paper 1614 covers bottom layer 1610 and covers all of the PET film sections 1626. An adhesive attaches the removable paper top surface to the polyimide tape A skin-facing surface, such that the user pulls the removable paper away from the bottom layer and in one motion removes the PET film pieces from electrodes 1620.

Patch 100 can also be made more comfortable by the addition of material between the top layer and the bottom layer, such as cushioning material that can cushion the electrodes and electronic components. The cushioning material may be disposed subjacent to the bottom layer and superjacent to the top layer, in at least a portion of patch 100. A cushioning material may include cellulosic fibers (e.g., wood pulp fibers), other natural fibers, synthetic fibers, woven or nonwoven sheets, scrim netting or other stabilizing structures, superabsorbent material, foams, binder materials, or the like, as well as combinations thereof.

Hydrogel Overlaps Electrode Edges

In some examples, each electrode 1620 is covered with hydrogel 1626 which conforms to the size of the electrode 1620, such that the edge of electrode 1620 is exposed to the user's skin when patch 100 is applied to the skin. This edge may abrade or cut the user's skin during the time when patch 100 is affixed to the skin.

In some examples, hydrogel 1626 is dimensioned so as to overlap the edges of electrode 1620. Hydrogel 1626 is placed over electrode 1620 with the accuracies of placement used in manufacturing, such that the edges of electrode 1620 is always covered with hydrogel 1626. This keeps the edge electrode 1620 from touching the user's skin. The risk of electrodes 1620 from abrading or cutting the user's skin is therefore eliminated.

Several examples are specifically illustrated and/or described herein. However, it will be appreciated that modifications and variations of the disclosed examples are covered by the above teachings and within the purview of the appended claims without departing from the spirit and intended scope of the invention.

What is claimed is:

1. A method of treating restless legs syndrome (RLS), the method comprising:
affixing a patch externally on a dermis of a user adjacent to a targeted nerve of the user, the patch comprising a flexible substrate, a processor directly coupled to the substrate, and electrodes directly coupled to the substrate;
detecting an occurrence of RLS; and
in response to the detecting, activating the patch, the activating comprising generating electrical stimuli via the electrodes that is directed to the targeted nerve, the activating further comprising:
determining a target charge level;
outputting a series of pulses from the electrodes;
for each pulse outputted, measuring a charge value of the pulse and compare the charge value to the target charge level;
if the charge value is greater than the target charge level, reducing a strength level of a subsequent outputted pulse;
if the charge value is less than the target charge level, increasing the strength level of a subsequent outputted pulse; and
repeating the determining, outputting and measuring.

2. The method of claim 1, the targeted nerve comprising an afferent nerve.

3. The method of claim 2, the afferent nerve comprising one of a peroneal nerve or a sural nerve.

4. The method of claim 1, the electrical stimuli comprising a series of pulses with a pattern comprising an intensity and a duration, further comprising adjusting the intensity or the duration of the pattern after each treatment for RLS.

5. The method of claim 1, the electrical stimuli comprising a series of pulses with a pattern, comprising pulse widths of 50-200 microseconds and voltage of 100-500 volts.

6. The method of claim 1, the patch comprising one or more sensors that measure biometrics of the user and based on the measurement adjusting the electrical stimuli.

7. The method of claim 1, the patch comprising one or more sensors in communication with a smart controller, the smart controller receiving data from the sensors and using the data to orient the patch relative to the user.

8. The method of claim 1, the determining the target charge level $Q_{target}$ comprises generating an acquisition series of pulses $$Q_{target} = \sum_{i=1}^{T*f} Q_{pulse}(i),$$

where T is a duration of the acquisition series of pulses, f is a count of pulses for one treatment acquisition series of pulses and $Q_{pulse}(i)$ is a measured charge of each of the acquisition series of pulses.

9. The method of claim 1, the patch further comprising electronic circuitry directly coupled to the substrate and comprising a differential integrator, the charge value of the pulse based on an output of the differential integrator.

10. The method of claim 1, the detecting the occurrence of RLS comprising monitoring muscle movement of a leg of the user.

11. A restless legs syndrome (RLS) treatment system comprising:
a patch adapted to be externally coupled on a dermis of a user adjacent to a targeted nerve of the user, the patch comprising a flexible substrate, a processor directly coupled to the substrate, and electrodes directly coupled to the substrate;
an RLS detector adapted to detect an occurrence of RLS; and
the processor adapted to activate the patch, the activating comprising generating electrical stimuli via the electrodes that is directed to the targeted nerve, the activating further comprising:
determining a target charge level;
outputting a series of pulses from the electrodes;
for each pulse outputted, measuring a charge value of the pulse and compare the charge value to the target charge level;
if the charge value is greater than the target charge level, reducing a strength level of a subsequent outputted pulse;
if the charge value is less than the target charge level, increasing the strength level of a subsequent outputted pulse; and
repeating the determining, outputting and measuring.

12. The system of claim 11, the targeted nerve comprising an afferent nerve.

13. The system of claim 12, the afferent nerve comprising one of a peroneal nerve or a sural nerve.

14. The system of claim 11, the electrical stimuli comprising a series of pulses with a pattern comprising an intensity and a duration, further comprising adjusting the intensity or the duration of the pattern after each treatment for RLS.

15. The system of claim 11, the electrical stimuli comprising a series of pulses with a pattern, comprising pulse widths of 50-200 microseconds and voltage of 100-500 volts.

16. The system of claim 11, the determining the target charge level $Q_{target}$ comprises generating an acquisition series of pulses and $$Q_{target} = \sum_{i=1}^{T*f} Q_{pulse}(i),$$

where T is a duration of the acquisition series of pulses, f is a count of pulses for one treatment acquisition series of pulses and $Q_{pulse}(i)$ is a measured charge of each of the acquisition series of pulses.

17. The system of claim 11, the patch further comprising electronic circuitry directly coupled to the substrate and comprising a differential integrator, the charge value of the pulse based on an output of the differential integrator.

18. The system of claim 11, the detecting the occurrence of RLS comprising monitoring muscle movement of a leg of the user.

* * * * *